US009248120B2

(12) United States Patent
Penny et al.

(10) Patent No.: US 9,248,120 B2
(45) Date of Patent: Feb. 2, 2016

(54) REVERSING INTESTINAL INFLAMMATION BY INHIBITING RETINOIC ACID METABOLISM

(75) Inventors: Hweixian Leong Penny, Singapore (SG); Edgar G. Engleman, Palo Alto, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 531 days.

(21) Appl. No.: 13/592,180

(22) Filed: Aug. 22, 2012

(65) Prior Publication Data

US 2013/0131129 A1 May 23, 2013

Related U.S. Application Data

(60) Provisional application No. 61/526,574, filed on Aug. 23, 2011.

(51) Int. Cl.
*A61K 31/428* (2006.01)
*A61K 31/4184* (2006.01)

(52) U.S. Cl.
CPC ........... *A61K 31/428* (2013.01); *A61K 31/4184* (2013.01)

(58) Field of Classification Search
CPC ......................... A61K 31/4184; A61K 31/428
USPC ......................................................... 514/367
See application file for complete search history.

(56) References Cited

U.S. PATENT DOCUMENTS

| | | | | |
|---|---|---|---|---|
| 6,486,187 | B1 | 11/2002 | Venet et al. | |
| 7,265,143 | B2 | 9/2007 | Njar et al. | |
| 7,807,650 | B2 * | 10/2010 | Jimenez et al. | 514/44 R |
| 2002/0193578 | A1 * | 12/2002 | Vasudevan et al. | 534/753 |
| 2004/0228871 | A1 * | 11/2004 | Hasan et al. | 424/178.1 |
| 2005/0187298 | A1 | 8/2005 | Vasudevan et al. | |
| 2006/0009645 | A1 * | 1/2006 | Smith et al. | 548/265.8 |
| 2008/0031984 | A1 | 2/2008 | Quart et al. | |
| 2010/0048415 | A1 | 2/2010 | Croner et al. | |
| 2010/0292284 | A1 | 11/2010 | Barrett et al. | |

OTHER PUBLICATIONS

Terzic et al.(Gastroenterology ,2010, 138, pp. 2101-2114).*

Collins; et al. "Retinoic acid attenuates ileitis by restoring the balance between T-helper 17 and T regulatory cells", Gastroenterology (Nov. 2011), 141(5):1821-1831.

Duester; et al. "Cytosolic retinoid dehydrogenases govern ubiquitous metabolism of retinol to retinaldehyde followed by tissue-specific metabolism to retinoic acid", Chem Biol Interact (Feb. 2003), 143-144:201-210.

Eisinger; et al. "Retinoic acid inhibits beta-catenin through suppression of Cox-2: a role for truncated adenomatous polyposis coli", J Biol Chem (Oct. 2007), 282(40):29394-29400.

(Continued)

*Primary Examiner* — Savitha Rao

(74) *Attorney, Agent, or Firm* — Bozicevic, Field & Francis LLP; Kyle A. Gurley

(57) ABSTRACT

An agent that increases local concentration of retinoic acid (RA) in the intestine through modifying enzymatic pathways involved in RA metabolism is administered in a dose effective to inhibit or reverse production of inflammatory mediators by intestinal dendritic cells and thereby reduce intestinal inflammation and tumor growth associated with intestinal inflammation.

8 Claims, 16 Drawing Sheets
(12 of 16 Drawing Sheet(s) Filed in Color)

(56) References Cited

OTHER PUBLICATIONS

Goss; et al. "Effects of liarozole fumarate (R85246) in combination with tamoxifen on N-methyl-N-nitrosourea (MNU)—induced mammary carcinoma and uterus in the rat model", BMC Cancer (Jan. 2007), 7:26.
Huynh; et al. "Inhibitory effects of retinoic acid metabolism blocking agents (RAMBAs) on the growth of human prostate cancer cells and LNCaP prostate tumour xenografts in SCID mice", Br J Cancer (Feb. 2006), 94(4):513-523.
Nadauld; et al. "Adenomatous polyposis coli control of C-terminal binding protein-1 stability regulates expression of intestinal retinol dehydrogenases", J Biol Chem (Dec. 2006), 281(49):37828-37835.
Patel; et al. "Novel retinoic acid metabolism blocking agents endowed with multiple biological activities are efficient growth inhibitors of human breast and prostate cancer cells in vitro and a human breast tumor xenograft in nude mice", J Med Chem (Dec. 2004), 47(27):6716-6729.
Rai; et al. "DNA demethylase activity maintains intestinal cells in an undifferentiated state following loss of APC", Cell (Sep. 2010), 142(6):930-942.
Shelton; et al. "Up-regulation of CYP26A1 in adenomatous polyposis coli-deficient vertebrates via a WNT-dependent mechanism: implications for intestinal cell differentiation and colon tumor development", Cancer Res (Aug. 2006), 66(15):7571-7577.
Verfaille; et al. "Oral R115866 in the treatment of moderate to severe facial acne vulgaris: an exploratory study", Br J Dermatol (Jul. 2007), 157(1):122-126.
Verfaille; et al. "Oral R115866 in the treatment of moderate to severe plaque-type psoriasis", J Eur Acad Dermatol Venereol (Sep. 2007), 21(8):1038-1046.
Xavier; et al. "Unravelling the pathogenesis of inflammatory bowel disease", Nature (Jul. 2007), 448(7152):427-434.
Bai; et al., "All-trans retinoic acid down-regulates inflammatory responses by shifting the Treg/Th17 profile in human ulcerative and murine colitis", Journal of Leukocyte Biology (Oct. 2009), 86(4):959-969.
Klopcic; et al., "Indomethacin and Retinoic Acid Modify Mouse Intestinal Inflammation and Fibrosis: A Role for SPARC", Dig. Dis Sci (Jun. 2008), 53(6):1553-1563.
Osanai; et al., "Cellular Retinoic Acid Bioavailability Determines Epithelial Integrity: Role of Retinoic Acid Receptor (alpha) Agonists in Colitis", Molecular Pharmacology (Jan. 2007), 71(1):250-258.

* cited by examiner a
WT LP
APC^Min/+ LP
MHC II
CD11c
2.22
7.66
b
% PI-Lin-
Spleen
mLN/PP
SI-LP
c
WT
APC^Min/+
SPL
mLN/PP
SI-LP
CD11b
CD103
43.8
40.3
9.22
49.4
18.7
26.6
5.46
2.63
34.5
57.5
8.59
6.39
43.5
41.5
58.4
21.7
1.42
60.4
18.9
3.24
d
% parent DC subset
CD11b+ CD103-
CD11b- CD103+
CD11b+ CD103+
e
IL-6
TNFα
IL-12p40
pg/ml a b c a
b
ADH I
ADH II
WT
APC$^{Min/+}$
Relative mRNA expression
10 wk
14 wk
18 wk
N.D.
SI-LP DC
spl DC
Epithelial cells
0.000
0.001
0.002
0.003
0.004
0.0000
0.0002
0.0004
0.0006
0.0008
0.0010
0.0
0.5
1.0
1.5
2.0
0.00
0.02
0.04
0.06
0.08 a
Retinyl Esters
nmol/g tissue
0
10
20
30
40
Duodenum
Jejunum
Ileum
Colon
Eye
b
Retinol
nmol/g tissue
0
1
2
3
4
5
Duodenum
Jenjunum
Ileum
Colon
Eye
*
***

REVERSING INTESTINAL INFLAMMATION BY INHIBITING RETINOIC ACID METABOLISM

GOVERNMENT RIGHTS

This invention was made with Government support under contract CA141468 awarded by the National Institutes of Health. The Government has certain rights in this invention.

BACKGROUND OF THE INVENTION

Pathological inflammation is emerging as an underlying mechanism for numerous diseases. For example, the major forms of idiopathic IBD, ulcerative colitis and Crohn's disease are chronic inflammatory disorders of the gastrointestinal tract. Animal studies have shown that chronic intestinal inflammation precipitates as well as propagates tumor growth.

A number of sentinel cell populations in the intestinal mucosa continuously monitor luminal microbes and other antigens. Among the subsets of antigen-presenting cells, myeloid-derived dendritic cells are a dominant subtype in the intestinal lamina propria and show considerable functional plasticity depending on the location, state of maturation, and stage of inflammation. Dendritic cells form an extensive network beneath the intestinal epithelium and project long processes through the interstices of epithelial cells to sample luminal antigens. In response to TLR ligands, immature dendritic cells produce IL-23, which contributes to development of intestinal inflammation in murine models of colitis and intestinal inflammation. The remarkable capacity of dendritic cells to orchestrate distinct immune responses is aided by a panoply of environmental cues, which condition the cells to adopt specific phenotypes in different settings. DCs in gut-associated lymphoid tissue are of particular interest because they maintain tolerance to commensal flora as well as mount protective inflammatory responses in the face of pathogen incursion.

Migration of innate immune cells such as neutrophils, macrophages, and dendritic cells into target mucosal tissues depends on the expression of cytokines, chemokines and adhesion molecules. Recruitment of activated neutrophils, dendritic cells and macrophages into the lamina propria in general amplifies the local immune response, whereas activated natural killer cell recruitment seems to enhance antimicrobial factors, leading to attenuation of inflammation.

The CD4 T-cell lineage (TH17) is characterized by the production of IL-17. Its development is promoted by IL-23, in addition to IL-6 and TGFbeta. Evidence indicates that RORct (retinoic acid-related orphan nuclear hormone receptor gamma-t) is necessary for TH17 commitment and differentiation. In addition to its ability to support the development of TH17 cells, IL-23 induces the secretion of IL-17 by non-T-cells in an inflammatory environment, and both T cells and monocytes serve as sources of increased expression in the mucosa of IBD patients.

An understanding and manipulation of inflammatory cells in the gut is of great interest. The present invention addresses this issue.

SUMMARY OF THE INVENTION

Methods are provided for reducing intestinal inflammation, particularly chronic inflammation, and tumor growth precipitated by intestinal inflammation. In the methods of the invention, an effective dose of an agent is provided to the individual, where the agent increases local concentration of retinoic acid (RA) in the intestine through modifying enzymatic pathways involved in RA metabolism.

In some embodiments, an inhibitor of CYP26A1 is administered in a dose effective form to neutralize a pre-existing inflammatory environment, prevent the development of inflammation, or maintain the tolerogenic functions of intestinal dendritic cells that maintain intestinal tolerance by inducing Treg formation. Alternatively, an agent that increases activity of retinaldehyde dehydrogenase or retinol dehydrogenase may be administered in a dose effective to neutralize or prevent inflammation in the intestine. The appropriate dose may be determined by evaluating the effect of the agent on functions of intestinal dendritic cells, for example by monitoring synthesis of cytokines such as IL-23 and IL-17, or by overall analysis of intestinal inflammation. The methods of the invention exclude administration of retinoic acid directly.

Dendritic cells are shown to be reprogrammed due to local loss of the vitamin A metabolite, retinoic acid (RA), which occurs as a result of insufficient retinaldehyde dehydrogenase and an overabundance of the transcriptional co-repressor, Ctbp1. The reprogrammed dendritic cells secrete mainly pro-inflammatory cytokines and induce Th17 formation. Treatment by the methods of the invention replenish RA and neutralize the inflammatory phenotype of the dendritic cells.

Other aspects and features will be readily apparent to the ordinarily skilled artisan upon reading the present disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is best understood from the following detailed description of exemplary embodiments when read in conjunction with the accompanying drawings. It is emphasized that, according to common practice, the various features of the drawings are not necessarily to-scale. On the contrary, the dimensions of the various features are arbitrarily expanded or reduced for clarity. Included in the drawings are the following figures.

μg/ml), R848 (10 μg/ml), CpG 2336 (10 μg/ml). Supernatants were collected after 48 hours. Representative bar graphs show mean production (with SEM) of the cytokines IL-6, TNFα and IL-2p40 as measured by standard ELISA. Data in (e) was obtained at late stage of disease. Data are representative of 4 independent experiments, with DCs pooled from 8 mice per strain (WT and $APC^{Min/+}$) per experiment. An unpaired student's t test with 95% confidence interval was performed. $P<0.05$=*; $p<0.001$=; $p<0.0001$=*.

Figure 2:
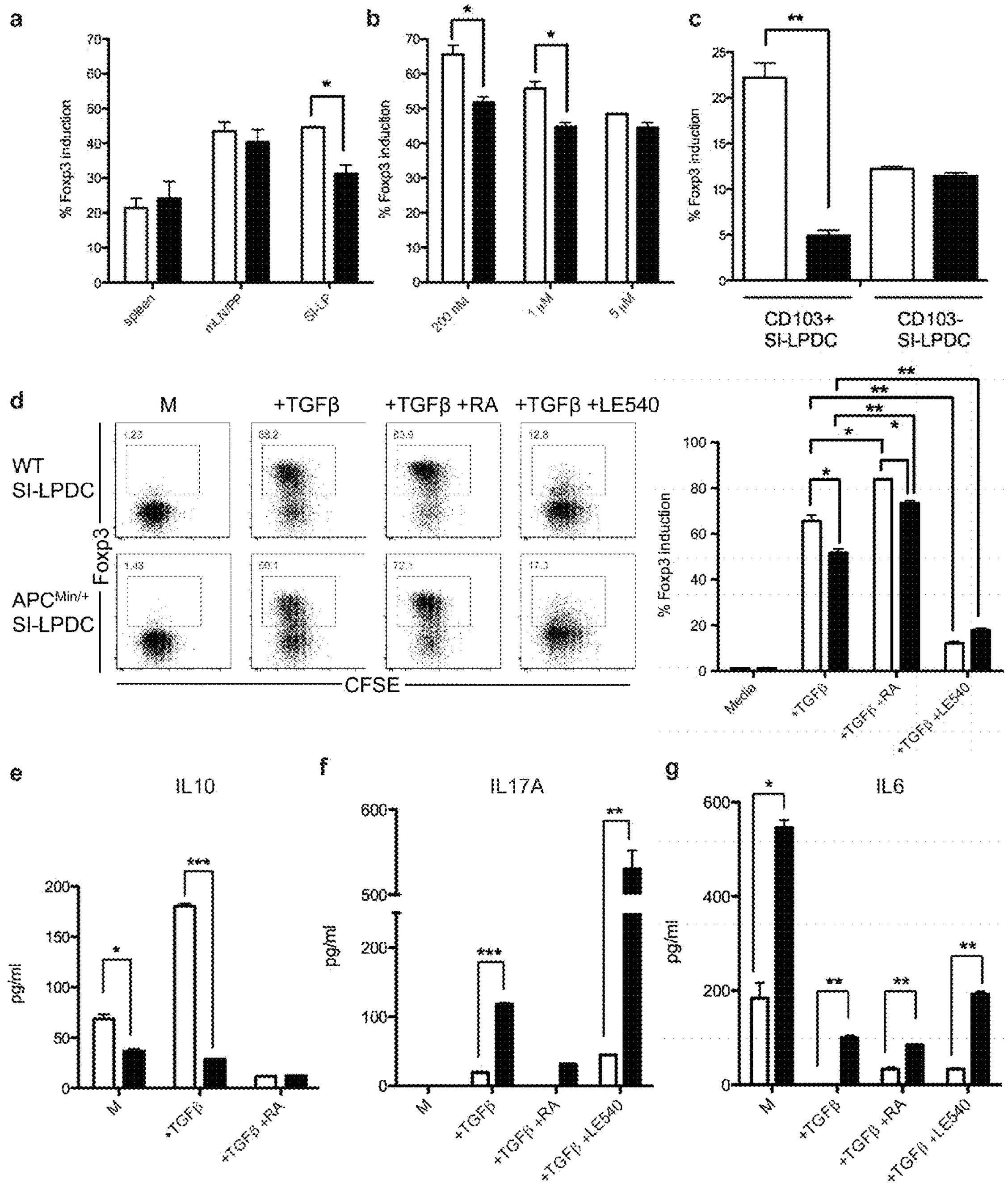

FIG. 2. $APC^{Min/+}$ SI-LPDCs have a reduced capacity to induce Foxp3+ $T_{Regs}$ and IL-10 producing CD4+ T cells, but instead generate Th17 cells, in an RA-dependent manner. $2\times10^4$ of sorted $CD11c^{hi}$ $MHCII^+$ DCs were co-cultured for 5 days with $1\times10^5$ MACS-enriched CD4+CD62L+Foxp3− naïve T cells from the spleen and lymph nodes of OT-II TCR-transgenic mice, along with $OVA_{323-339}$ peptide and 10 ng/ml recombinant human TGF-β. 5 ng/ml of recombinant human IL-2 was added to the cultures every other day beginning on day 2. □ WT; ■ $APC^{Min/+}$ (a) DCs used in these cultures were purified from SPL, mLN/PP and SI-LP, and stimulated with 5 nM $OVA_{323-339}$. Representative bar graph shows the mean frequency (with SEM) of Foxp3 induction from 9 independent experiments, with DCs pooled from at least 5 WT and at least 3 $APC^{Min/+}$ mice per experiment. (b) SI-LPDCs were used in these co-cultures, and stimulated with 200 nM, 1 μM and 5 μM $OVA_{323-339}$. Representative bar graph shows the mean frequency (with SEM) of Foxp3 induction from 4 independent experiments, with DCs pooled from at least 5 WT and at least 3 $APC^{Min/+}$ mice per experiment. (c) CD11c+ MHCII+ SI-LP DCs were further sorted into the CD103+ and CD103− subsets and cultured with naïve CD4 T cells as before. Bar graph shows the mean frequency (with SEM) of Foxp3 induction in a representative experiment of 2 independent experiments, with DCs pooled from at least 5 WT and at least 3 $APC^{Min/+}$ mice per experiment. (d) In these experiments, 10 nM all-trans RA or 1 of the RAR antagonist LE540 was added to whole SI-LPDC-T cell co-culture wells, in addition to TGF-β1. Cells were re-stimulated on day 4 with plate-bound anti-CD3 and anti-CD28 (1 μg/ml each) for 18 hours. Supernatants were collected on day 5 to assay for cytokine production by standard ELISA. Representative bar graphs show the mean production (with SEM) of IL10 (e), IL17A (f) and IL6 (g). Data in this figure were obtained at late stage disease, and are representative of 4 independent experiments, with DCs pooled from at least 5 WT and at least 3 $APC^{Min/+}$ mice per experiment. An unpaired student's t test with 95% confidence interval was performed. $P<0.05$=*; $p<0.001$=; $p<0.0001$=*.

Figure 3:
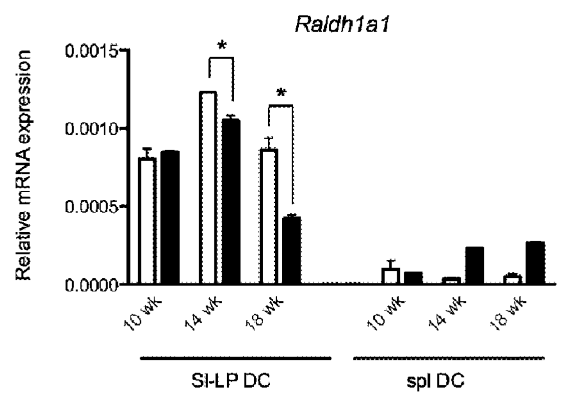
Figure 3:
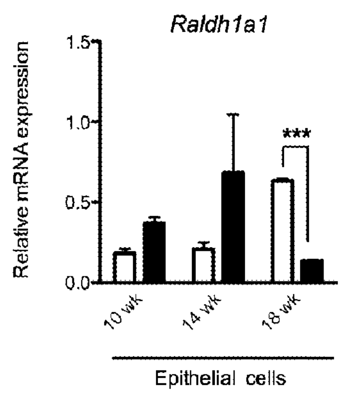
Figure 3:
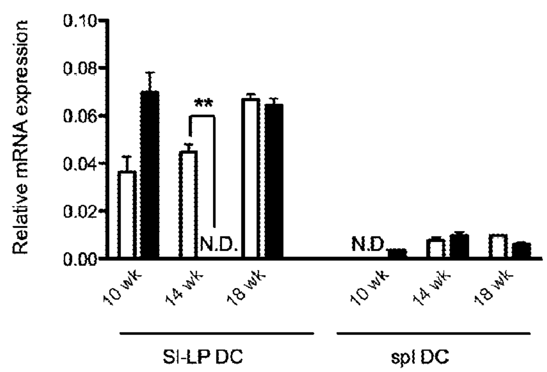
Figure 3:
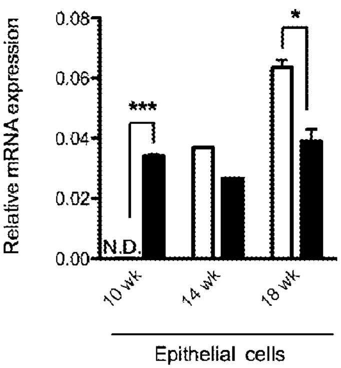
Figure 3:
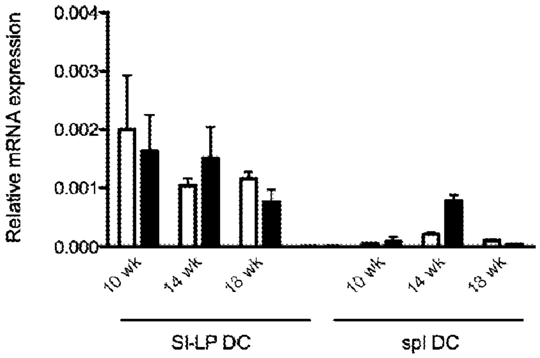
Figure 3:
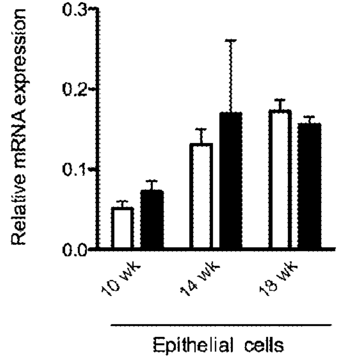
Figure 3:
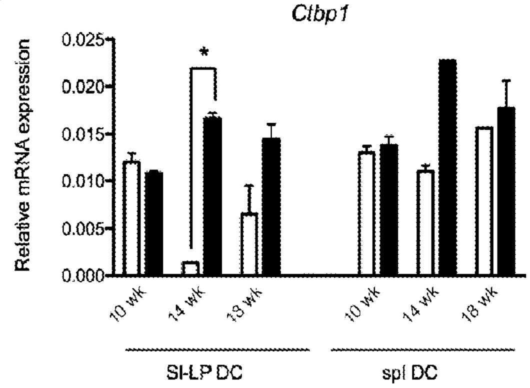
Figure 3:
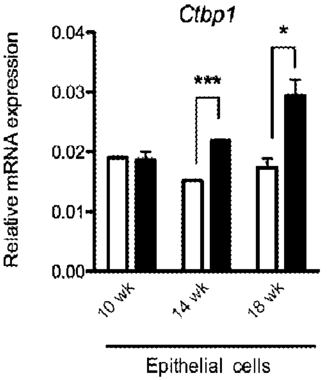

FIG. 3. $APC^{Min/+}$ SI-LP DCs and IECs have lower expression of Raldhs than WT, resulting in loss of RA in the tumor milieu. □ WT; ■ $APC^{Min/+}$ Total RNA from FACS-purified SI-LP DCs, splenic DCs (A) and epithelial cells (IECs) (B) was extracted and assayed in triplicate by qPCR for the genes Raldh1a1, Raldh1a2, Raldh1a3 and Ctbp1 (C). Each sample was normalized to ubiquitin b expression. Representative bar graphs show mean relative expression (with SEM) of triplicate samples. Data are representative of 3 independent qPCR experiments, with DCs and IECs pooled from 3 sorts per timepoint, using at least 5 WT and at least 3 $APC^{Min/+}$ mice per sort. An unpaired student's t test with 95% confidence interval was performed. $P<0.05$=*; $p<0.001$=; $p<0.0001$=*.

Figure 4:
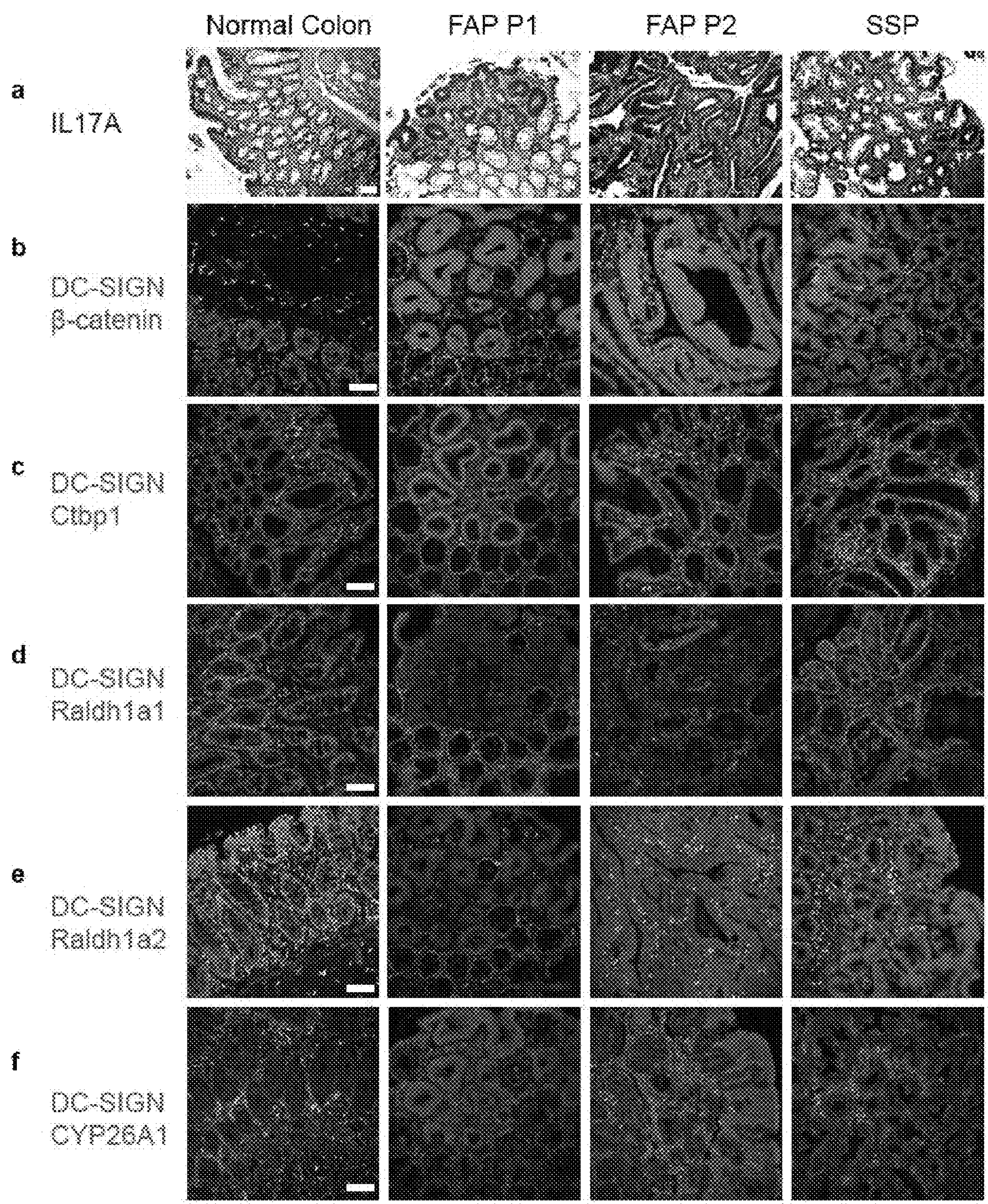

FIG. 4. FAP adenoma tissue exhibits IL-17-driven inflammation and loss of RA. Normal colon, FAP adenoma and sessile serrated polyp (SSP) sections were stained by immunohistochemistry for IL-17A (a) or co-stained by immunofluorescence with DC-SIGN and 8-catenin (b), Ctbp1 (c), Raldh1a1 (d), Raldh1a2 (e), CYP26A1 (f). Shown are samples from one representative normal colon, two representative FAP adenoma and one representative SSP patient. Images for FAP P1 show serial sections of the same polyp with underlying adjacent normal grossly uninvolved tissue. Overall, samples from a total of 11 normal colon, 8 FAP adenoma, 2 FAP adenocarcinoma and 4 SSP patients were analyzed. All images were captured using the same exposure time and the same brightfield or fluorescence settings for each protein of interest. White magnification bars in (a-f) are 100 μM.

Figure 5:
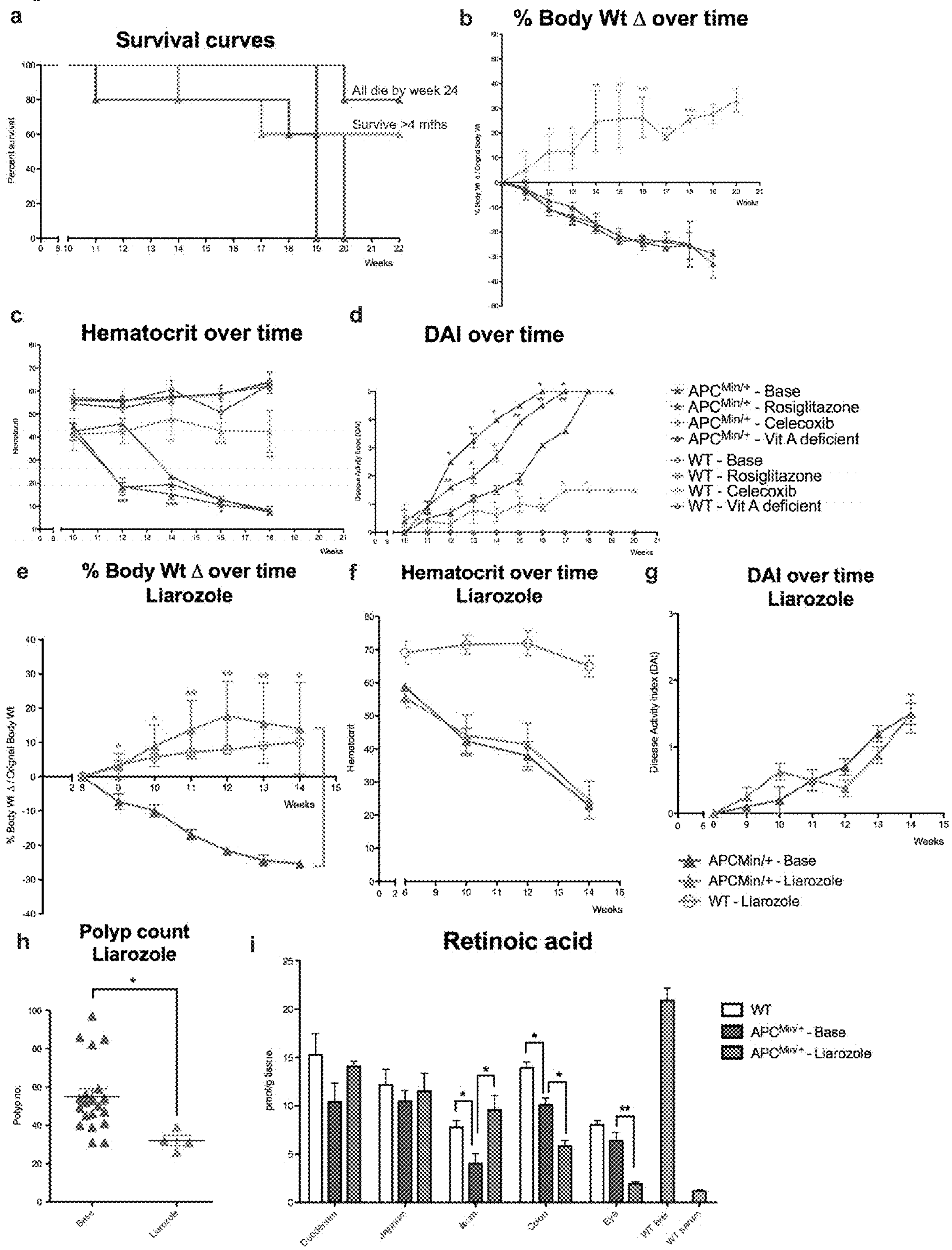

FIG. 5. A vitamin A-deficient diet exacerbates disease in $APC^{Min/+}$ mice. (a-d) 10 week old WT (open circles) and $APC^{Min/+}$ (filled triangles) mice were placed on 1500 ppm Celecoxib ( , ); 100 ppm Rosiglitazone ( , ); a vitamin A deficient diet (0 IU/g of vitamin A) ( , ); or a base diet (4 IU/g of vitamin A) ( , ) for 10 consecutive weeks. Mice were monitored for disease progression on the basis of hematocrit and body weight change. Line graphs show Kaplan-Meier survival curves (a), mean change in percentage body weight over original body weight (b) and hematocrits (c), with SEMs. 5 mice were used per strain for each diet. Data are representative of 2 independent experiments. Liarozole, a CYP26A1 inhibitor, ameliorates disease in $APC^{Min/+}$ mice by increasing local RA which reverses the SI-LPDC pro-inflammatory phenotype. 8 week old WT and $APC^{Min/+}$ mice were placed on 40 ppm of Liarozole for 6 consecutive weeks. $APC^{Min/+}$-Base diet ; $APC^{min/+}$-Liarozole ; WT-Liarozole . Disease was monitored as described in (a-d). In these experiments, small intestinal polyps were enumerated at 14 weeks, the point of euthanasia. A scatter plot shows the mean number of polyps (with SEM) (h) between $APC^{Min/+}$ mice on Liarozole compared to base diet. 5 mice were used per strain in each diet. Data are representative of 2 independent experiments. Significance in disease indicators of the different diets was calculated by comparing values to those obtained on the base diet. For calculating significance in DAI, a Wilcoxon-rank-sum test was used. (i) All-trans retinoic acid (RA) was extracted from the duodenum, jejunum, ileum, colon and eye and quantified by tandem mass spectrometry. WT-base diet □; $APC^{Min/+}$-Base diet ▨; $APC^{Min/+}$-Liarozole ▨. Bar graphs show mean amounts of retinoic acid per gram tissue (with SEM) among mice of the same strain. 5 WT, 5 $APC^{Min/+}$ and 4 Liarozole-treated $APC^{Min/+}$ mice were used in this experiment. For data in this figure, an unpaired student's t test with 95% confidence interval was performed unless otherwise stated. $P<0.05$=*; $p<0.001$=; $p<0.0001$=*. 8 week-old WT and $APC^{Min/+}$ mice were placed on 40 ppm of Liarozole for 6 consecutive weeks as described in FIG. 5. WT-base diet □; $APC^{Min/+}$-Base diet ▨; $APC^{Min/+}$-Liarozole ▨. (a) At the 14 week time point of euthanasia, $2\times10^4$ FACS-purified WT and $APC^{Min/+}$ SI-LPDCs were stimulated with Pam3Csk4 (1 μg/ml), LPS (10 μg/ml) and R848 (10 μg/ml). Supernatants were collected after 48 hours. Representative bar graphs show mean production (with SEM) of the cytokines IL-6, TNFα and IL-2p40 as measured by standard ELISA. Data are representative of 2 independent experiments, with at least 2 mice per strain. (b) A $T_{Reg}$ induction assay was performed as described in FIG. 2 on SI-LPDCs sorted from these mice. Representative bar graph shows the mean frequency (with SEM) of Foxp3 induction from 2 independent experiments, with DCs pooled from at least 2 mice per strain. (c) T cells in the SI-LPDC-T cell co-culture was re-stimulated as described in FIG. 2 and assayed for IL10, IL17A and IL6 by standard ELISA as before. For data in this figure, an unpaired student's t test with 95% confidence interval was performed. P<0.05=*; p<0.001=; p<0.0001=*.

Figure 6:
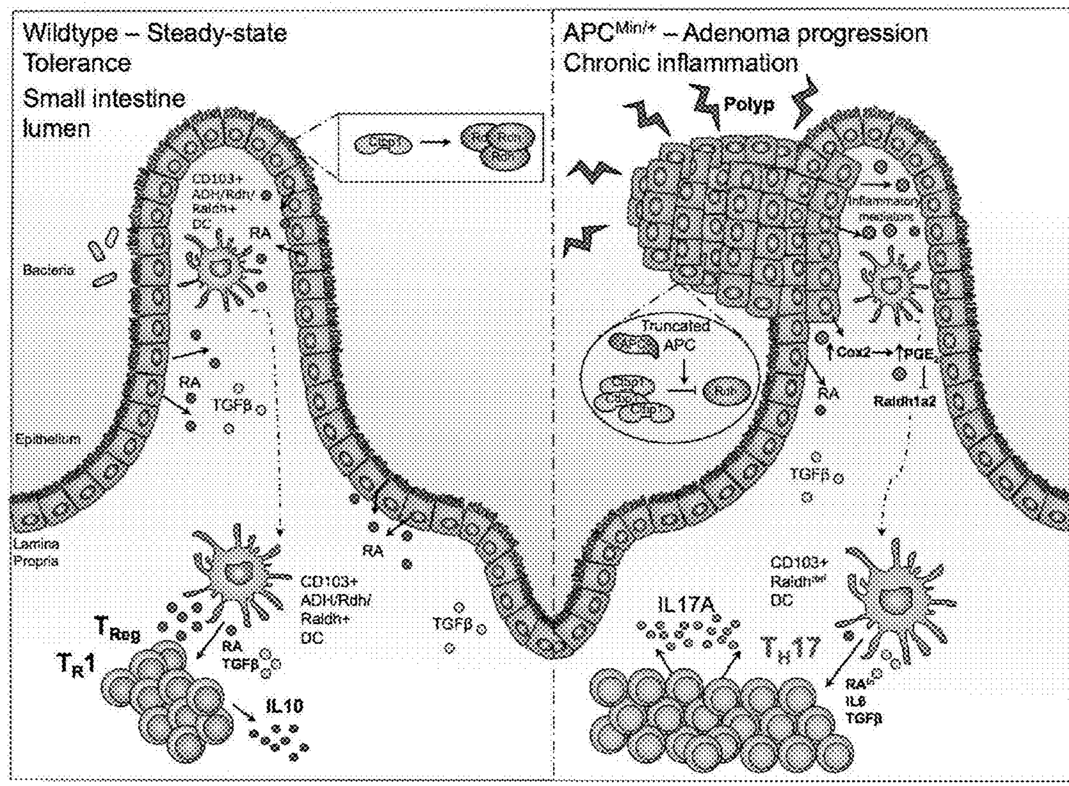

FIG. 6. Proposed Model: In the $APC^{Min/+}$ mouse, the immune state of the intestine, departs from homeostatic tolerance to chronic inflammation. Truncated APC protein leads to an accumulation of the transcription factor Ctbp1, which in turns suppresses retinol dehydrogenases in the epithelium and may lead to a reduction in local concentrations of RA. Upregulation of Cox2 in the inflamed tissue leads to greater production of $PGE_2$, which has been reported to suppress Raldh1a2 in DCs and likely does so to the surrounding epithelium as well. Lack of RA in the intestinal milieu conditions or 'reprograms' SI-LPDCs to a pro-inflammatory phenotype, in which IL6 production combined with TGFβ found locally, contributes to a deleterious Th17 response that promotes tumor growth.

Figure 7:
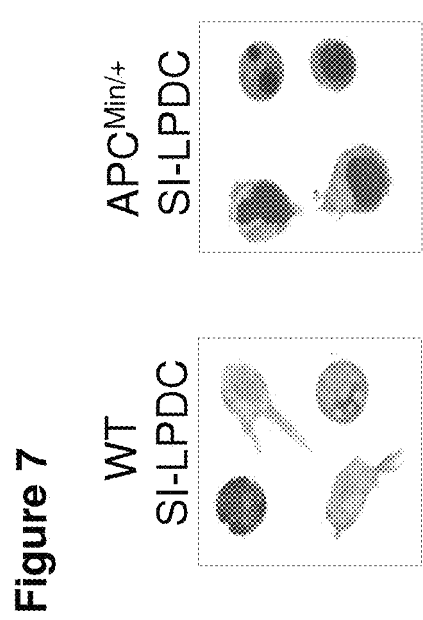

FIG. 7 Morphology of sorted SI-LPDCs from WT and $APC^{Min/+}$ mice. Sorted PI-EpCAM− CD45+ DX5− CD3e− CD19−≥$CD11c^{hi}$ MHCII+ LP DCs were stained with May Grumwald-Giemsa.

Figure 8:
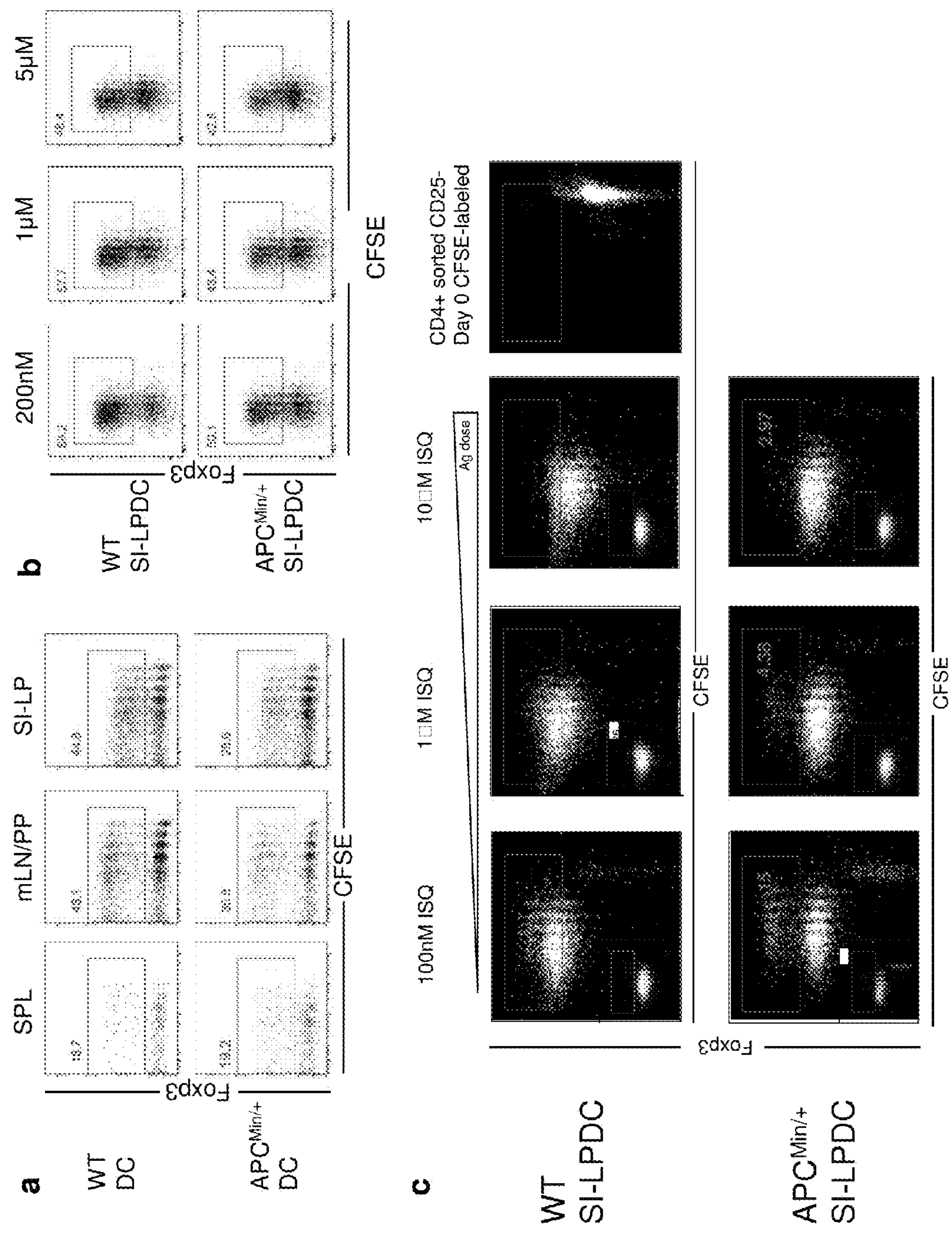

FIG. 8. $APC^{Min/+}$ SI-LPDCs have a reduced capacity to induce Foxp3+ $T_{Regs}$ in a tissue-specific, dose-dependent and time-dependent manner. A $T_{Reg}$ induction assay was performed as described in FIG. 2. (a-c) Representative dot plots of Foxp3 versus CFSE in Thy1.2+ CD4+ cells. The inset values of the bordered population show the mean frequency of Foxp3+ cells as a percentage of Thy1.2+ CD4+ cells. (a) DCs used in these cultures were purified from SPL, mLN/PP and SI-LP. (b) SI-LPDCs were incubated with 200 nM, 1 μM and 5 μM $OVA_{323-339}$. (c) SI-LPDCs were isolated from early, intermediate and late stage disease.

Figure 9:
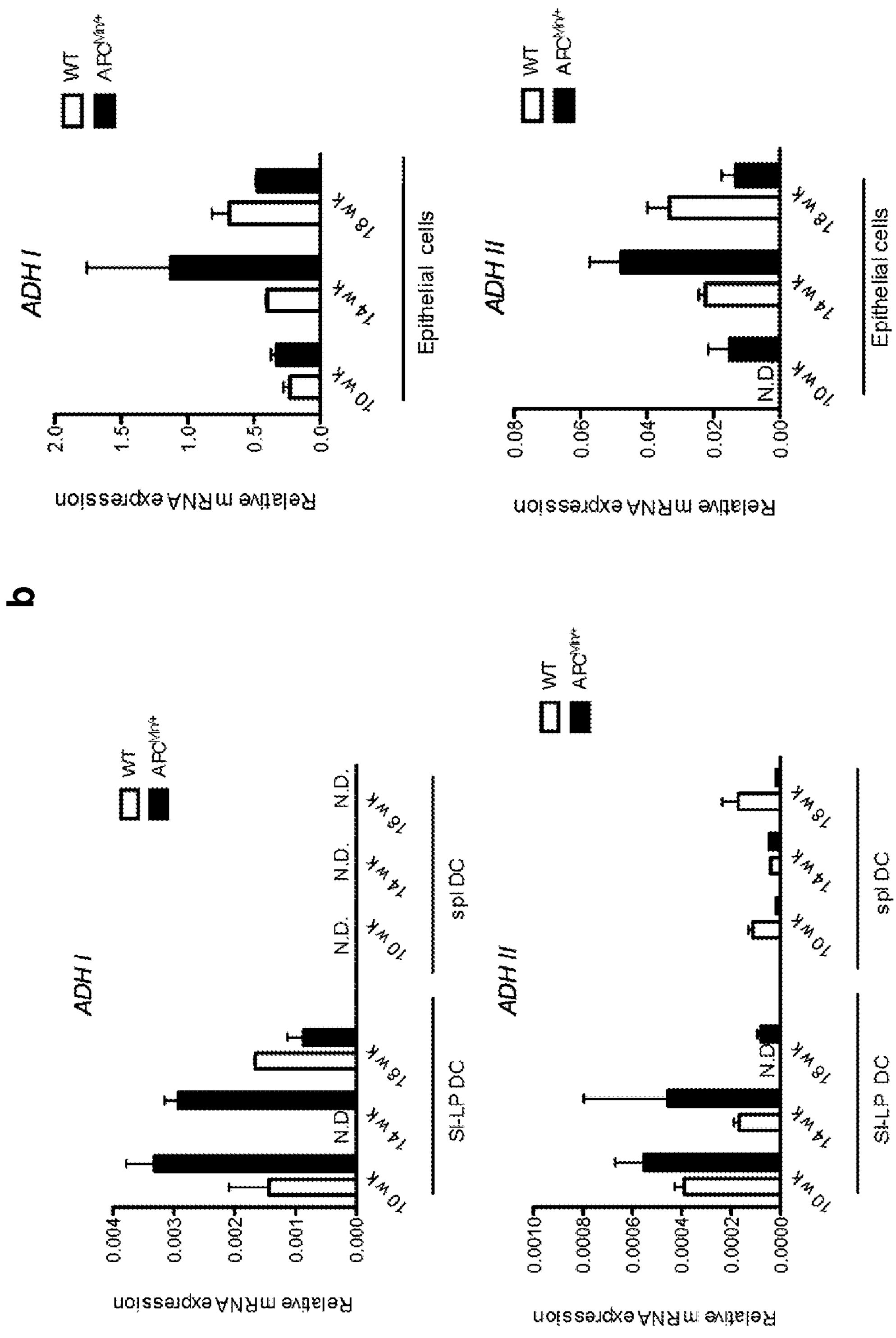

FIG. 9. ADH class I and II expression in $APC^{Min/+}$ IECs and SI-LPDCs increased at intermediate stage and decreased at subsequent late stage compared to WT counterparts. RT-qPCR on FACS-purified WT and $APC^{Min/+}$ SI-LP DCs, splenic DCs (a) and epithelial cells (IECs) (b) was performed as described in FIG. 3. ▭ WT; ▬ $APC^{Min/+}$ Representative bar graphs show mean relative expression (with SEM) of triplicate samples. Data are representative of 3 independent qPCR experiments, with DCs and IECs pooled from 3 sorts per time point, using at least 5 WT and at least 3 $APC^{Min/+}$ mice per sort. Shown is the ADH class I and II expression in DCs (a) and in IECs (b).

Figure 10:
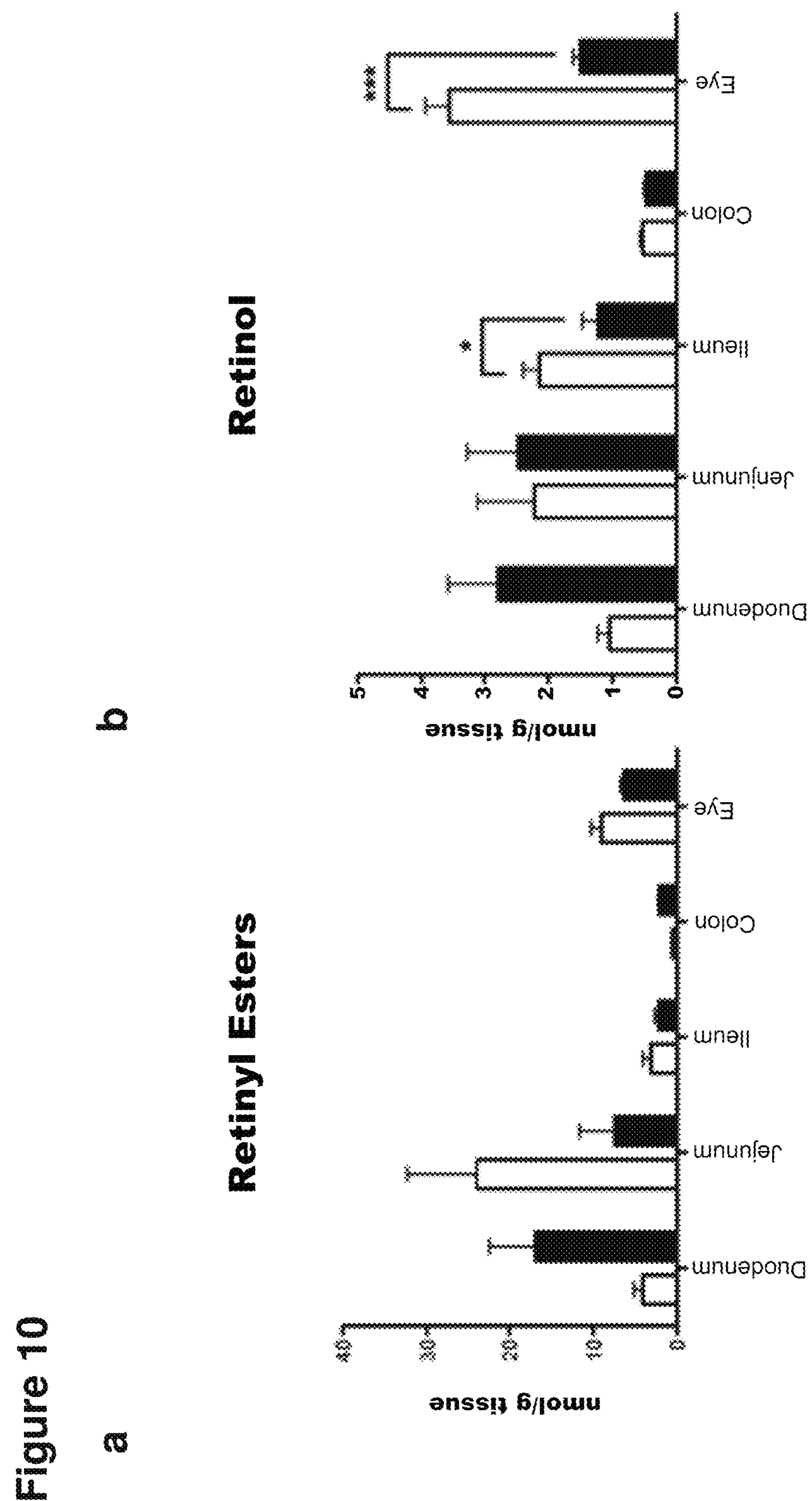

FIG. 10. Quantification of retinyl esters and retinol in vivo. Retinyl esters (RE) and all-trans retinol (ROL) were extracted from the duodenum, jejunum, ileum, colon and eye and quantified by HPLC. Bar graphs show mean amounts of retinoid per gram tissue (with SEM) among mice of the same strain. 5 WT, 5 $APC^{Min/+}$ and 4 Liarozole-treated $APC^{Min/+}$ mice were used in this experiment. An unpaired student's t test with 95% confidence interval was performed. P<0.05=*; p<0.001=; p<0.0001=*.

FIG. 11. Isotype control for immunohistochemistry and immunofluorescence. Normal colon sections were stained with an isotype control (Rabbit IgG) to the rabbit primaries used against β-catenin, Ctbp1, Raldh1a1. Raldh1a2 and CYP26A1.

Figure 12:
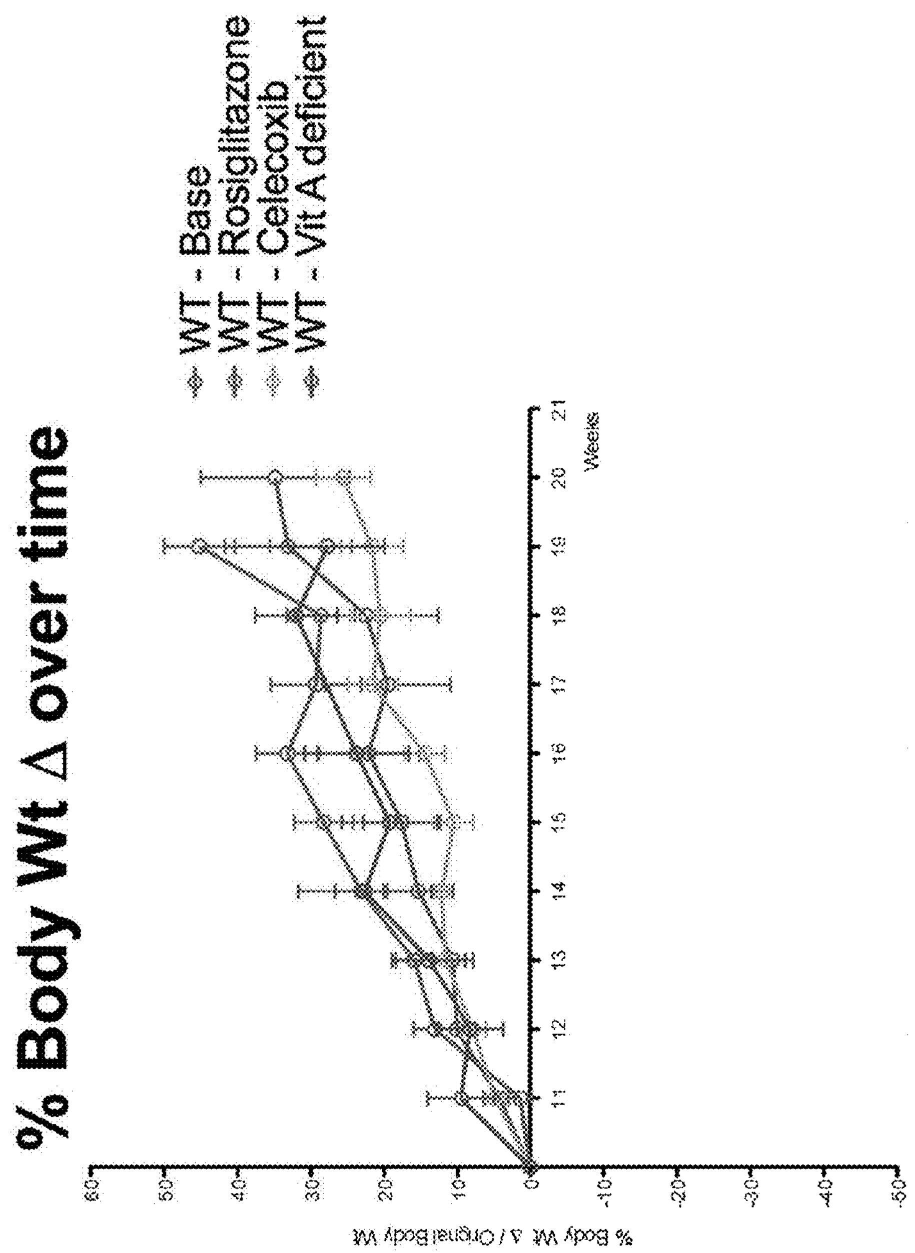

FIG. 12. Wildtype mice on base, rosiglitazone, celecoxib and vitamin A-deficient diets gain in weight comparably. Wildtype mice on the various diets 10 week-old WT mice were placed on 1500 ppm Celecoxib, 100 ppm Rosiglitazone, a vitamin A deficient diet (0 IU/g of vitamin A), or on a base diet (4 IU/g of vitamin A), for 10 consecutive weeks. Line graph show mean change in percentage body weight over original body weight. Data are representative of 2 independent experiments.

Figure 13:
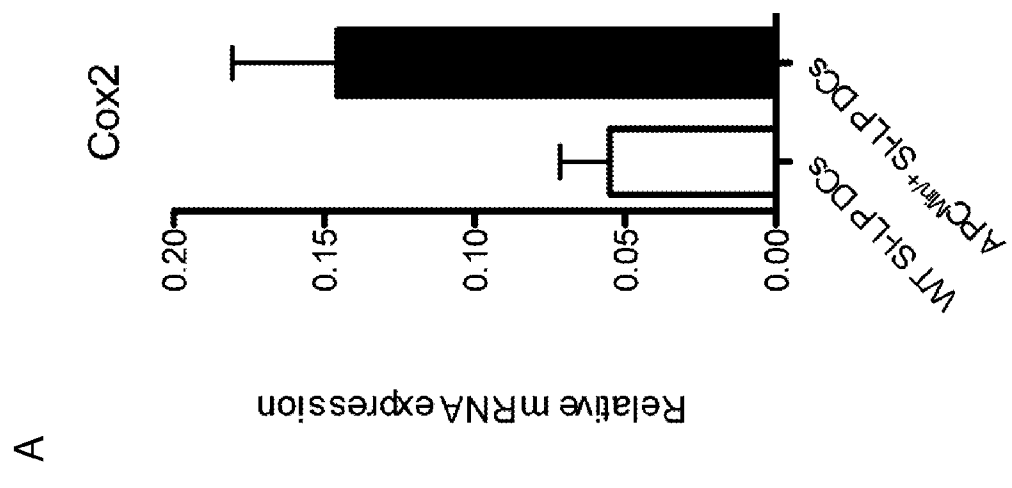

FIG. 13. $APC^{Min/+}$ SI-LPDCs display higher expression of Cox2 compared to WT SI-LPDCs. RT-qPCR on FACS-purified WT and $APC^{Min/+}$ SI-LP DCs was performed as described in FIG. 3. ▭ WT; ▬ $APC^{Min/+}$ Representative bar graph shows mean relative expression (with SEM) of triplicate samples. Data is from 1 independent qPCR experiment, with DCs and pooled from 3, using at least 5 WT and at least 3 $APC^{Min/+}$ mice per sort.

Figure 1:
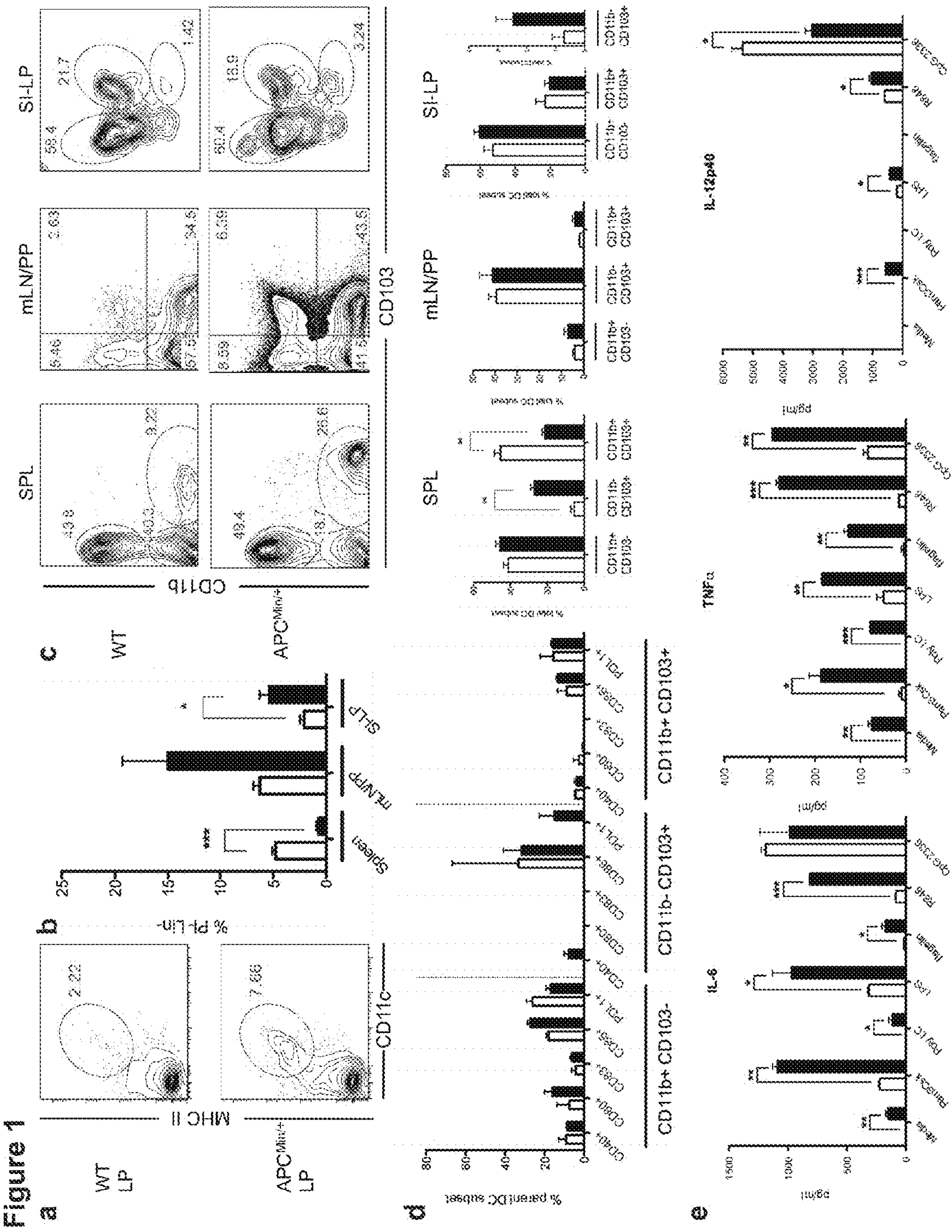
FIG. 1. $APC^{Min/+}$ SI-LPDCs accumulate over time and secrete more pro-inflammatory cytokines compared to WT SI-LPDCs upon TLR stimulation. DCs were defined as PI-EpCAM− CD45+ DX5− CD3e− CD19− $CD11c^{hi}$ MHCII+ in all the tissues. ▭ WT; ▬ $APC^{Min/+}$ (a) A representative contour plot depicting how DCs are gated by CD11c and MHC II expression. (b) A bar graph of the mean frequency (with SEM) of CD11c+ MHCII+ DCs as a percentage of PI-Lineage− cells. (c) Representative contour plots of SPL, mLN/PP and SI-LP DCs divided by CD11b and CD103 expression. Below each FACS plot are bar graphs showing the mean frequency (with SEM) of each subset in that tissue as a percentage of total CD11c+ MHCII+ DCs. (d) Mean frequency (with SEM) of cells expressing the co-stimulatory molecules CD40, CD80, CD83, CD86 and PDL1 as a percentage of the different CD11b CD103 subsets. Data for (a-d) were obtained at intermediate stage disease. Inset values in the contour plots are the mean frequencies of each population pooled using at least 4 mice per strain (WT and $APC^{Min/+}$) per experiment, from 5 independent experiments. (e) $5\times10^4$ FACS-purified WT and $APC^{Min/+}$ SI-LPDCs were stimulated with a panel of 6 different TLR agonists—Pam3Csk4 (1 μg/ml), Poly I:C (10 μg/ml), LPS (10 μg/ml), flagellin (1
Figure 14:
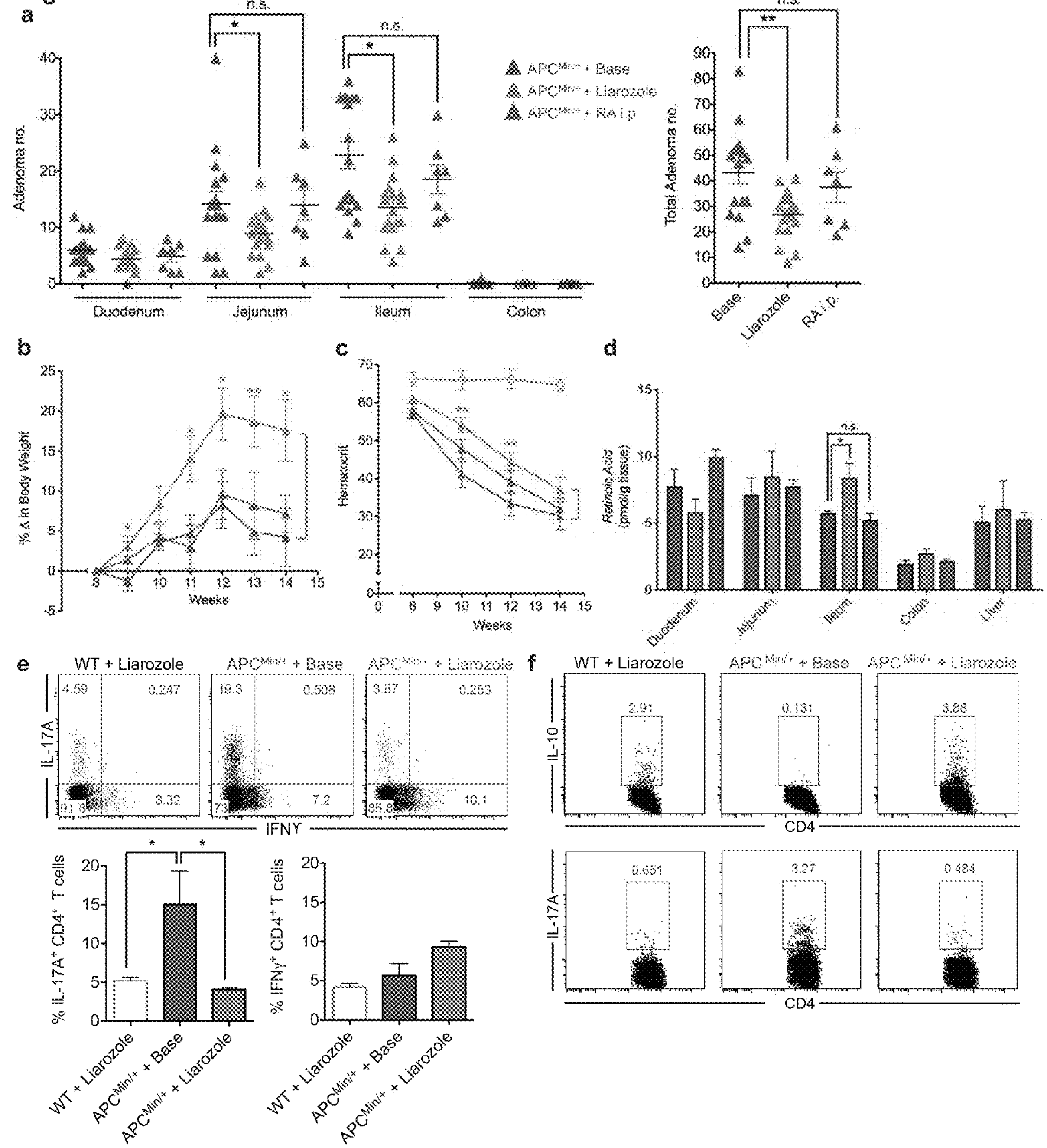

FIG. 14. Direct supplementation of RA does not affect tumor frequency or intestinal RA levels in $APC^{Min/+}$ mice, but Liarozole, a CYP26A1 inhibitor, improves all tested disease parameters. Groups of 8 week-old $APC^{Min/+}$ mice were injected i.p. with or without 200 μg/mouse RA in sunflower oil injected twice weekly while on a base diet, or placed on 40 ppm of Liarozole for 6 consecutive weeks. $APC^{Min/+}$ on Base diet/; $APC^{Min/+}$ on Liarozole/; $APC^{Min/+}$ given RA i.p./; WT on Liarozole. (a) Small intestine tumors were enumerated at 14 weeks. Scatter plot shows the mean number of tumors (with SEM) in $APC^{Min/+}$ mice on base, Liarozole or RA i.p. (a). Line graphs show mean change in percentage body weight (b) and hematocrit (c). For (a-c), data for mice on base diet and Liarozole are aggregated from 4 independent experiments, with at least 4 mice per group, while data for RA i.p.-injected mice are aggregated from 2 independent experiments, with at least 3 mice per group. (d) Concomitant to experiments performed in FIG. 4*d*, RA was quantified by LC/MS in 5 Liarozole treated and 5 RA i.p.-injected $APC^{Min/+}$ mice. Shown are mean RA levels (with SEM) in each tissue isolated at the 14 week time point. (e) Dot plots show the mean frequency of IL-17A- and IFNγ-producing $CD4^+$ T cells in freshly-isolated SI-LP from WT, $APC^{Min/+}$ and Liarozole-treated $APC^{Min/+}$ mice. Also shown are bar graphs depicting mean frequency (with SEM) of IL-17A- and IFNγ-producing CD4+ T cells from these mice. (f) CD103− SI-LPDCs from WT, $APC^{Min/+}$ and Liarozole-treated $APC^{Min/+}$ mice were co-cultured in the T cell differentiation assays performed as in FIG. 1. Inset values on the representative dot plots show the mean frequency of IL-10- and IL-17A-producing $CD4^+$ T cells induced. In (ef) $IL\text{-}17A^+$, $IFN\gamma^+$, or $IL\text{-}10^+$ cells are shown as a percentage of $CD4^+$ T cells. Data in (e-f) are from 2 independent experiments, with at least 4 mice per group. DCs obtained in (f) were pooled from all mice in the same group in each experiment. P<0.05=*; p<0.001=; p<0.0001=*.

Figure 15:
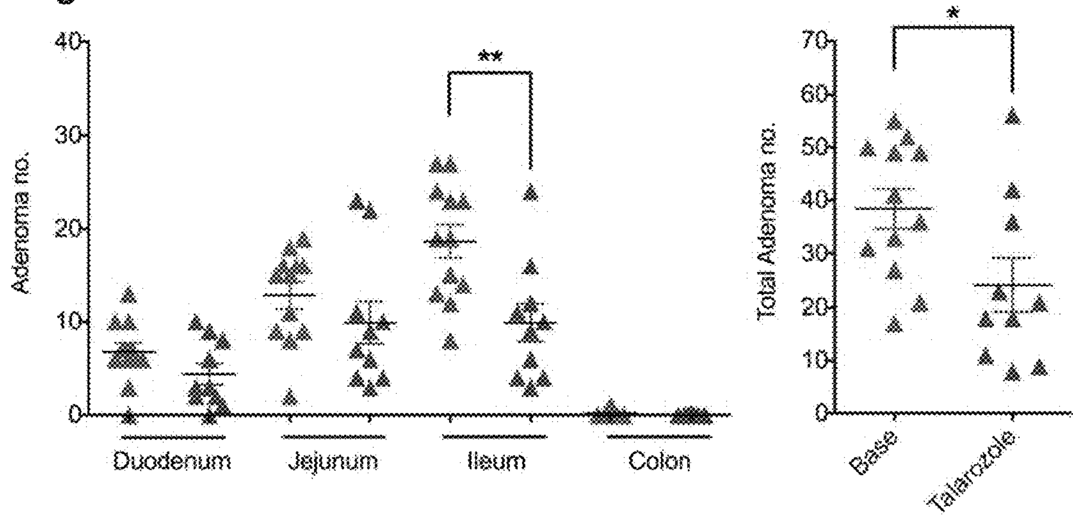

FIG. 15. Talarozole, a highly specific inhibitor of CYP26A1, ameliorates disease in $APC^{Min/+}$ mice. 8 week-old $APC^{Min/+}$ mice were placed on 8 ppm of Talarozole for 6 consecutive weeks. $APC^{Min/+}$-Base diet; $APC^{Min/+}$-Talarozole. At 14 weeks, tumors in the small and large intestine were enumerated. Results shown are aggregated from 2 independent experiments, with 5 mice per group.

Figure 16:
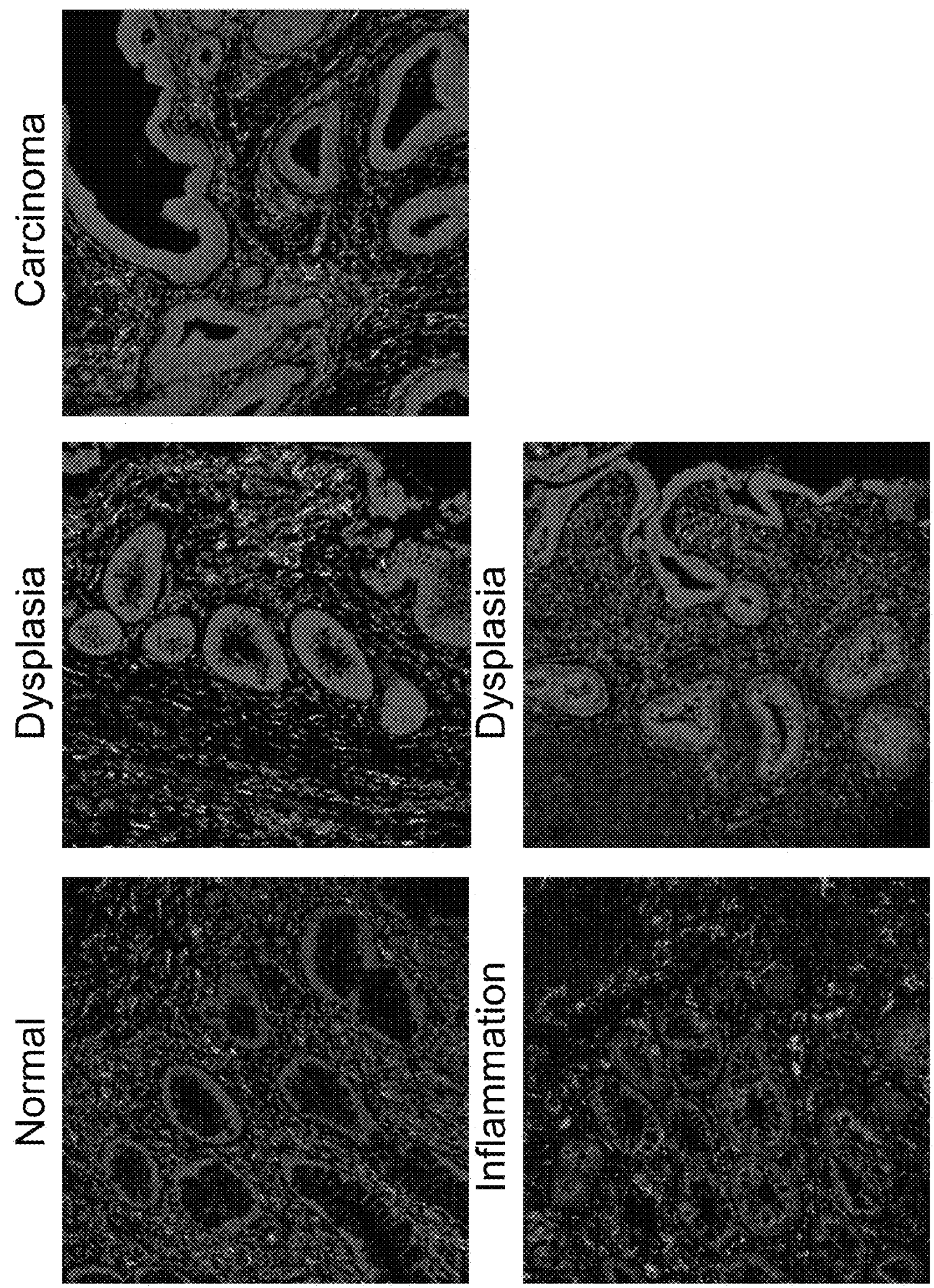

FIG. 16. Paraffin embedded normal, inflamed, dysplastic or carcinoma colon sections were stained by immunofluorescence for CYP26A1 (in red) and DC-SIGN (in green). Shown are samples from 2 different patients. Patient 1: Normal, Dysplastic and Carcinoma sections from a colectomy sample and Patient 2 Inflamed and dysplastic regions from a colectomy sample. All images were captured using the same exposure time and the same brightfield or fluorescence settings for each protein of interest. Similar results were obtained from staining with Raldh1a1 and Raldh1a2.

DETAILED DESCRIPTION OF THE EMBODIMENTS

It is to be understood that the invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the polypeptide" includes reference to one or more polypeptides and equivalents thereof known to those skilled in the art, and so forth.

It is further noted that the claims may be drafted to exclude any element which may be optional. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the disorder being treated and the general state of the patient's own immune system.

"Polypeptide" and "protein" as used interchangeably herein, can encompass peptides and oligopeptides. Where "polypeptide" is recited herein to refer to an amino acid sequence of a naturally-occurring protein molecule, "polypeptide" and like terms are not necessarily limited to the amino acid sequence to the complete, native amino acid sequence associated with the recited protein molecule, but instead can encompass biologically active variants or fragments, including polypeptides having substantial sequence similarity or sequence identify relative to the amino acid sequences provided herein. In general, fragments or variants retain a biological activity of the parent polypeptide from which their sequence is derived.

As used herein, "polypeptide" refers to an amino acid sequence of a recombinant or non-recombinant polypeptide having an amino acid sequence of i) a native polypeptide, ii) a biologically active fragment of an polypeptide, or iii) a biologically active variant of an polypeptide. Polypeptides suitable for use can be obtained from any species, e.g., mammalian or non-mammalian (e.g., reptiles, amphibians, avian (e.g., chicken)), particularly mammalian, including human, rodenti (e.g., murine or rat), bovine, ovine, porcine, murine, or equine, particularly rat or human, from any source whether natural, synthetic, semi-synthetic or recombinant. In general, polypeptides comprising a sequence of a human polypeptide are of particular interest.

The term "derived from" indicates molecule that is obtained directly from the indicated source (e.g., when a protein directly purified from a cell, the protein is "derived from" the cell) or information is obtained from the source, e.g. nucleotide or amino acid sequence, from which the molecule can be synthesized from materials other than the source of information.

The term "isolated" indicates that the recited material (e.g, polypeptide, nucleic acid, etc.) is substantially separated from, or enriched relative to, other materials with which it occurs in nature (e.g., in a cell). A material (e.g., polypeptide, nucleic acid, etc.) that is isolated constitutes at least about 0.1%, at least about 0.5%, at least about 1% or at least about 5% by weight of the total material of the same type (e.g., total protein, total nucleic acid) in a given sample.

The terms "subject" and "patient" are used interchangeably herein to mean a member or members of any mammalian or non-mammalian species that may have a need for the pharmaceutical methods, compositions and treatments described herein. Subjects and patients thus include, without limitation, primate (including humans), canine, feline, ungulate (e.g., equine, bovine, swine (e.g., pig)), avian, and other subjects. Humans and non-human animals having commercial importance (e.g., livestock and domesticated animals) are of particular interest. As will be evidence from the context in which the term is used, subject and patient refer to a subject or patient susceptible to infection by a Flaviviridae virus, particularly HCV.

"Mammal" means a member or members of any mammalian species, and includes, by way of example, canines; felines; equines; bovines; ovines; rodentia, etc. and primates, particularly humans. Non-human animal models, particularly mammals, e.g. primate, murine, lagomorpha, etc. may be used for experimental investigations.

The term "unit dosage form," as used herein, refers to physically discrete units suitable as unitary dosages for human and animal subjects, each unit containing a predetermined quantity of compounds calculated in an amount sufficient to produce the desired effect in association with a pharmaceutically acceptable diluent, carrier or vehicle. The specifications for the novel unit dosage forms depend on the particular compound employed and the effect to be achieved, and the pharmacodynamics associated with each compound in the host.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes both one and more than one such excipient, diluent, carrier, and adjuvant.

As used herein, a "pharmaceutical composition" is meant to encompass a composition suitable for administration to a subject, such as a mammal, especially a human. In general a "pharmaceutical composition" is sterile, and is usually free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal and the like.

T helper 17 cells (Th17) are a subset of T helper cells, characterized by their production of interleukin 17 (IL-17). They are considered developmentally distinct from Th1 and Th2 cells and excessive amounts of the cell are thought to play a key role in autoimmune disease. In humans, a combination of TGF-β, IL-1β and IL-23 induces Th17 differentiation from naive T cells. Both interferon gamma (IFNγ) and IL-4, the main stimulators of Th1 and Th2 differentiation respectively, negatively regulate Th17 differentiation.

T helper 1 cells (Th1). Proliferating helper T cells that develop into effector T cells differentiate into two major subtypes of cells known as Th1 and Th2 cells. Th1 cells primarily produce IFN-γ and TNF-β cytokines. IFN-γ increases the production of interleukin-12 by dendritic cells and macrophages, and via positive feedback, IL-12 stimulates the production of IFN-γ in helper T cells, thereby promoting the Th1 profile. IFN-γ also inhibits the production of cytokines such as IL-4. Conditions that polarize to the TH1 type include antigen presenting cells and IL-12.

Interleukin-17 (IL-17) refers to a group of cytokines called the IL-17 family. IL-17 shows high homology to viral IL-17 encoded by an open reading frame of the T lymphotropic rhadinovirus Herpesvirus saimiri. To elicit its functions, IL-17 binds to a type I cell surface receptor called IL-17R of which there are at least three variants IL17RA, IL17RB, and IL17RC. Members of the IL-17 family include IL-17B, IL-17C, IL-17D, IL-17E (also called IL-25), and IL-17F. All members of the IL-17 family have a similar protein structure, with four highly conserved cysteine residues critical to their 3-dimensional shape, although with no sequence similarity to any other known cytokines. Numerous immune regulatory functions have been reported for the IL-17 family.

IL-23 alpha subunit is a protein encoded by the IL23A gene (see Oppmann et al. (2001) *Immunity* 13 (5): 715-25). This gene encodes the p19 subunit of the heterodimeric cytokine interleukin 23 (IL23). IL23 is composed of this protein and the p40 subunit of interleukin 12. The receptor of IL23 is formed by the beta 1 subunit of IL12 (IL12RB1) and an IL23 specific subunit, IL23R. Both IL23 and IL12 can activate the transcription activator STAT4, and stimulate the production of interferon-gamma (IFNG). In contrast to IL12, which acts mainly on naive CD4(+) T cells, IL23 preferentially acts on memory CD4(+) T cells.

Dendritic cell. As used herein, the term refers to any member of a diverse population of morphologically similar cell types found in lymphoid or non-lymphoid tissues. Dendritic cells are a class of "professional" antigen presenting cells, and have a high capacity for sensitizing MHC-restricted T cells. Dendritic cells may be recognized by function, or by phenotype, particularly by cell surface phenotype. These cells are characterized by their distinctive morphology, intermediate to high levels of surface MHC-class II expression and ability to present antigen to T cells, particularly to naive T cells (Steinman et al. (1991) Ann. Rev. Immunol. 9:271; incorporated herein by reference for its description of such cells).

The vitamin A metabolite all-trans-retinoic acid (RA) is an essential signaling molecule in embryonic development and throughout life; a potent regulator of cell differentiation, proliferation, and apoptosis in various cell types. RA acts through specific RA nuclear receptors (RARα, β, and γ) and their heterodimeric counterparts, the retinoid-X-receptors (α, β, and γ) to positively or negatively regulate expression of RA target genes by binding to their respective response elements. Vitamin A deficiency has been linked to increased susceptibility to carcinogenesis in animal models. Although essentially all cell types express nuclear retinoic acid receptors, cellular responsiveness is determined by RA bioavailability regulated by the coordinated balance between vitamin A nutritional status and RA biosynthesis and catabolism. The RA-metabolizing cytochrome P450s CYP26A1, B1, and C1 convert RA into rapidly excreted oxoderivatives (4-OH RA, 4-oxo RA, 18-OH RA), while retinaldehyde dehydrogenase generates RA. Inhibitors of the CYP26 gene family are of interest for use in the methods of the invention, including without limitation CYP26A1.

CYP26A1 is a member of the cytochrome P450 superfamily of enzymes. The cytochrome P450 proteins are monooxygenases. This endoplasmic reticulum protein acts on retinoids, including all-trans-retinoic acid (RA), with both 4-hydroxylation and 18-hydroxylation activities. Two alternatively spliced transcript variants of this gene, which encode the distinct isoforms, have been reported.

Inhibitors of CYP26A1 can increase local concentrations of RA. For example, an orally administered inhibitor, particularly a formulation that provides for enteric delivery, can raise the RA concentration in intestinal tissues. Inhibitors of CYP26A1 are known in the art, and include, without limitation, talarozole, ketoconazole; liarozole; [S—(R*,R*)]—N-[4-[2-(dimethylamino)-1-(1H-imidazole-1-yl)propyl]-phenyl]2-benzothiazolamine (R116010); (R)—N-[4-[2-ethyl-1-(1H-1,2,4-triazol-1-yl)butyl]phenyl]-2-benzothiazolamine (R115866); the retinoic acid receptor (RAR)γ agonist CD1530; the pan-RAR agonist 4-[(E)-2-(5,6,7,8-tetrahydro-5,5,8,8-tetramethyl-2-naphthalenyl)-1-propenyl]benzoic acid; peroxisome proliferator-activated receptor ligands rosiglitazone and pioglitazone; etc.

Aldehyde dehydrogenase 1 (retinal dehydrogenase, RALDH1) is a liver cytosolic isoform of acetaldehyde dehydrogenase. Retinaldehyde is generated by ADH1 from retinol, and its concentration is determined in large part by its subsequent catabolism by RALDH1 to retinoic acid, see Hempel et al. (1984) Europ. J. Biochem. 141: 21-35; Hsu et al. (1985) Proc. Nat. Acad. Sci. 82: 3771-3775. Agonists of RALDH1, or other agents that increase activity of RALDH1 are of interest for the methods of the invention.

Retinol dehydrogenase 10 (RDH10) generates all-trans retinal from all-trans retinol and may plan an important role in the photic visual cycle. The first oxidative step of vitamin A metabolism is catalyzed in large part by RDH10 and is critical for spatiotemporal synthesis of retinoic acid, Sandell et al. (2007) Genes Dev. 21: 1113-1124; Wu et al. (2002) Invest. Ophthal. Vis. Sci. 43: 3365-3372. Agonists of RDH10, or other agents that increase activity of RDH10 are of interest for the methods of the invention.

The term colorectal cancer includes all cancers of the colon and/or rectum, but particularly adenocarcinoma of the colon (e.g., mucinous (colloid) adenocarcinoma or signet ring adenocarcinoma). Other types of colorectal cancer included by the term include the following varieties of colon cancer: neuroendocrine, lymphoma, melanoma, squamous cell, sarcoma and carcinoid. The term colorectal cancer also includes all stages of colorectal cancer; for example, under the Modified Duke Staging System or TNM system (Tumor, Node, Metastasis). The stages associated with these systems are well known by practitioners of ordinary skill in the art.

In the methods of the invention, the agent(s) may be administered to a subject to treat an inflammatory condition, which inflammation may predispose to colorectal cancer, and may include individuals having familial adenomatous polyposis (FAP), hereditary nonpolyposis colon cancer (HNPCC) (i.e., Lynch I Syndrome or Lynch II Syndrome), inflammatory bowel disease, such as chronic ulcerative colitis (UC) or Crohn's disease, other family cancer syndromes (e.g., Peutz-Jegher Syndromem and Familial Juvenile Polyposis), adenomatous polyps (e.g., sessile (flat with a broad base and no stalk); tubular (composed of tubular glands extending downward from the outer surface of the polyp); villous (composed of fingerlike epithelial projections extending outward from the surface of the bowel mucosa); pedunculated (attached by a narrow base and a long stalk), and sporadic forms of colon cancer.

Familial adenomatous polyposis (FAP) is an inherited condition in which numerous polyps form mainly in the epithelium of the large intestine. In general, while these polyps start out benign, malignant transformation into colon cancer occurs when not treated. Familial juvenile polyposis (FJP) is an autosomal dominant condition characterized by multiple juvenile polyps of the gastrointestinal (GI) tract. Kindreds have been described in which there is involvement of the colon only, the upper GI tract or both upper and lower GI tracts. FJP is a hamartomatous polyposis syndrome. Adenomatous polyps (adenomas) of the colon and rectum may be benign (noncancerous) growths that may be precursor lesions to colorectal cancer. In general, polyps greater than one centimeter in diameter are associated with a greater risk of cancer. If polyps are not removed, they typically continue to grow and can become cancerous.

Crohn's Disease (Regional Enteritis; Granulomatous Ileitis or Ileocolitis) is a chronic transmural inflammatory disease that usually affects the distal ileum and colon but may occur in any part of the GI tract. Symptoms include diarrhea and abdominal pain. Abscesses, internal and external fistulas, and bowel obstruction may arise. Extraintestinal symptoms, particularly arthritis, may occur. Diagnosis is by colonoscopy and barium contrast studies. The most common initial presentation is chronic diarrhea with abdominal pain, fever, anorexia, and weight loss. The abdomen is tender, and a mass or fullness may be palpable. Gross rectal bleeding is unusual except in isolated colonic disease, which may manifest similarly to ulcerative colitis. Some patients present with an acute abdomen that simulates acute appendicitis or intestinal obstruction. About 33% of patients have perianal disease (especially fissures and fistulas), which is sometimes the most prominent or even initial complaint. In children, extraintestinal manifestations frequently predominate over GI symptoms; arthritis, fever of unknown origin, anemia, or growth retardation may be a presenting symptom, whereas abdominal pain or diarrhea may be absent.

Established Crohn's disease is rarely cured but is characterized by intermittent exacerbations and remissions. Some patients suffer severe disease with frequent, debilitating periods of pain. However, with judicious medical therapy and, where appropriate, surgical therapy, most patients function well and adapt successfully. Disease-related mortality is very low. GI cancer, including cancer of the colon and small bowel, is the leading cause of excess Crohn's disease-related mortality.

Irritable bowel syndrome consists of recurring upper and lower GI symptoms, including variable degrees of abdominal pain, constipation or diarrhea, and abdominal bloating. Diagnosis is clinical. Treatment is generally symptomatic, consisting of dietary management and drugs, including anticholinergics and agents active at serotonin receptors. There are no consistent motility abnormalities. Some patients have an abnormal gastro-colonic reflex, with delayed, prolonged colonic activity. There may be reduced gastric emptying or disordered jejunal motility. Some patients have no demonstrable abnormalities, and in those that do, the abnormalities may not correlate with symptoms. Small-bowel transit varies: sometimes the proximal small bowel appears to be hyperreactive to food or parasympathomimetic drugs. Intraluminal pressure studies of the sigmoid show that functional constipation can occur with hyperreactive haustral segmentation (ie, increased frequency and amplitude of contractions). In contrast, diarrhea is associated with diminished motor function. Thus strong contractions can, at times, accelerate or delay transit.

Diagnosis is based on characteristic bowel patterns, time and character of pain, and exclusion of other disease processes through physical examination and routine diagnostic tests. Diagnostic testing should be more intensive when "red flags" are present: older age, weight loss, rectal bleeding, vomiting. Proctosigmoidoscopy with a flexible fiberoptic instrument should be performed. Introduction of the sigmoidoscope and air insufflation frequently trigger bowel spasm and pain. The mucosal and vascular patterns in IBS usually appear normal. Colonoscopy is preferred for patients >40 with a change in bowel habits, particularly those with no previous IBS symptoms, to exclude colonic polyps and tumors. In patients with chronic diarrhea, particularly older women, mucosal biopsy can rule out possible microscopic colitis.

METHODS OF THE INVENTION

Methods are provided for reducing intestinal inflammation, particularly chronic inflammation, and tumor growth precipitated by intestinal inflammation. In the methods of the invention, an effective dose of an agent is provided to the individual, where the agent increases local concentration of retinoic acid (RA) in the intestine through modifying enzymatic pathways involved in RA metabolism. In particular, an inhibitor of a CYP26, enzyme, for example CYP26A1, may be administered in a dose effective to neutralize an inflammatory environment and/or maintain the tolerogenic functions of intestinal dendritic cells that maintain intestinal tolerance by inducing Treg formation. Alternatively, an agent that increases activity of retinaldehyde dehydrogenase or retinol dehydrogenase may be administered in a dose effective to maintain the tolerogenic functions of dendritic cells. The appropriate dose may be determined by evaluating the effect of the agent on functions of dendritic cells, or by overall analysis of intestinal inflammation. The methods of the invention exclude administration of retinoic acid directly. The administration of inhibitors of CYP26A1, including without limitation liarozole and talarozole, are of particular interest.

The term "therapeutically effective amount" or "therapeutically effective dosage" may mean that amount or dosage of an agent or combination thereof of the invention or composition thereof that will elicit a biological or medical response of a tissue, system, patient, subject or host that is being sought by the administrator (such as a researcher, doctor or veterinarian) which includes any measurable alleviation of the signs, symptoms and/or clinical indicia of intestinal inflammation, including colorectal cancer (e.g., tumor growth and/or metastasis) including the prevention, slowing or halting of progression of the inflammation to any degree whatsoever.

Dosage regimens may be adjusted to provide the optimum desired response (e.g., a therapeutic response). For example, a single dose may be administered or several divided doses may be administered over time or the dose may be proportionally reduced or increased as indicated by the exigencies or the particular circumstances or requirements of the therapeutic situation. For example, dosage may be determined or adjusted, by a practitioner of ordinary skill in the art (e.g., physician or veterinarian) according to the patient's age, weight, height, past medical history, present medications and the potential for cross-reaction, allergies, sensitivities and adverse side-effects. For example, the physician or veterinarian could start doses of the agent at levels lower than that required in order to achieve the desired therapeutic effect and gradually increase the dosage until the desired effect is achieved. The effectiveness of a given dose or treatment regimen of an agent of the invention can be determined, for example, by determining the concentration of pro-inflammatory cytokines such as IL-23; whether a tumor being treated in the subject shrinks or ceases to grow. The size and progress of a tumor can be easily determined, for example, by X-ray, magnetic resonance imaging (MRI) or visually in a surgical procedure. In general, tumor size and proliferation can be measured by use of a thymidine PET scan (see e.g., Wells et al., Clin. Oncol. 8: 7-14 (1996)). Generally, the thymidine PET scan includes the injection of a radioactive tracer, such as [2-$^{11}$C]-thymidine, followed by a PET scan of the patient's body (Vander Borght et al., Gastroenterology 101: 794-799, 1991; Vander Borght et al., J. Radiat. Appl. Instrum. Part A, 42: 103-104 (1991)). Other tracers that can be used include [$^{18}$F]-FDG (18-fluorodeoxyglucose), [$^{124}$I]IUdR (5-[$^{124}$I]iodo-2'-deoxyuridine), [$^{76}$Br]BrdUrd (Bromodeoxyuridine), [$^{18}$F]FLT (3'-deoxy-3' fluorothymidine) or [$^{11}$C]FMAU (2'-fluoro-5-methyl-1-β-D-arabinofuranosyluracil).

Methods for treating or preventing intestinal inflammation, including inflammation leading to colorectal cancer by administering a pharmaceutical composition comprising an agent that increases RA levels by altering enzymatic activity involved in RA metabolism, in association with a pharmaceutically acceptable carrier are also within the scope of the present invention (e.g., in a single composition or separately in a kit) as are combinations and compositions including such pharmaceutical compositions. The pharmaceutical compositions may be prepared by any methods well known in the art of pharmacy; see, e.g., Gilman, et al., (eds.) (1990), The Pharmacological Bases of Therapeutics, 8th Ed., Pergamon Press; A. Gennaro (ed.), Remington's Pharmaceutical Sciences, 18th Edition, (1990), Mack Publishing Co., Easton, Pa.; Avis, et al., (eds.) (1993) Pharmaceutical Dosage Forms: Parenteral Medications Dekker, N.Y.; Lieberman, et al., (eds.) (1990) Pharmaceutical Dosage Forms: Tablets Dekker, N.Y.; and Lieberman, et al., (eds.) (1990), Pharmaceutical Dosage Forms: Disperse Systems Dekker, N.Y.

A pharmaceutical composition can be prepared using conventional pharmaceutically acceptable excipients and additives and conventional techniques. Such pharmaceutically acceptable excipients and additives include non-toxic compatible fillers, binders, disintegrants, buffers, preservatives, anti-oxidants, lubricants, flavorings, thickeners, coloring agents, emulsifiers and the like. All routes of administration are contemplated including, but not limited to, parenteral (e.g., subcutaneous, intravenous, intraperitoneal, intramuscular, topical, intraperitoneal, inhalation, intra-cranial) and non-parenteral (e.g., oral, transdermal, intranasal, intraocular, sublingual, rectal and topical).

Oral administration is of interest, including enteric formulations, which may include acid stable agents that maintain activity under gastrointestinal conditions, enteric coatings of pills, and the like, where there is a significant activity of the agent in intestinal tissues.

Injectables can be prepared in conventional forms, either as liquid solutions or suspensions, solid forms suitable for solution or suspension in liquid prior to injection, or as emulsions. The injectables, solutions and emulsions can also contain one or more excipients. Excipients include, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

In an embodiment of the invention, pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include sodium chloride injection, Ringers Injection, isotonic dextrose Injection, sterile water injection, dextrose and lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations may be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcellulose, hydroxypropyl methylcellulose and polyvinylpyrrolidone. Emulsifying agents include Polysorbate 80 (TWEEN-80). A sequestering or chelating agent of metal ions includes EDTA (ethylenediaminetetraacetic acid) or EGTA (ethylene glycol tetraacetic acid). Pharmaceutical carriers may also include ethyl alcohol, polyethylene glycol and propylene glycol for water miscible vehicles; and sodium hydroxide, hydrochloric acid, citric acid or lactic acid for pH adjustment.

In an embodiment of the invention, preparations for parenteral administration can include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

The concentration of the agent of the invention, which is optionally in association with a further chemotherapeutic agent, can be adjusted so that a dose provides an effective amount to produce the desired pharmacological effect. As discussed herein, the exact dose depends, in part, on the age, weight and condition of the patient or animal as is known in the art.

Implantation of a slow-release or sustained-release system, such that a constant level of dosage is maintained, is also contemplated herein. Briefly, an active agent is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, or ethylene/vinyloxyethanol copolymer, that is insoluble in body fluids. The antibody or fragment diffuses through the outer polymeric membrane in a release rate controlling step. The percentage of active agent contained in such parenteral compositions is highly dependent on the specific nature thereof, as well as the activity of the antibody or antigen-binding fragment, which is optionally in association with a further chemotherapeutic agent, and the needs of the subject.

Agents set forth herein can be formulated into a sustained release formulation including liposomal formulations such as unilamellar vesicular (ULV) and multilamellar vesicular (MLV) liposomes.

Example 1

The present invention is intended to exemplify the present invention and not to be a limitation thereof. Methods and compositions disclosed below fall within the scope of the present invention.

In the majority of sporadic colorectal cancers and in FAP, tumorigenesis is initiated from mutations that arise in the APC tumor suppressor gene. In the $APC^{Min/+}$ murine model, numerous adenomas develop in the intestines, closely resembling FAP. $APC^{Min/Min}$ homozygotes die in utero, and $APC^{Min/+}$ heterozygotes spontaneously lose their wildtype allele during puberty and start developing polyps by week 10. Although these mice do not develop invasive metastases, they eventually succumb to a fatal anemia through excessive intestinal bleeding.

Prior studies in $APC^{Min/+}$ mice show that chronic intestinal inflammation precipitates as well as propagates tumor growth and that Th17 cells are the responsible immune effector cells. Since chronic inflammation in the intestine predisposes to colorectal cancer, it is surprising that the role of local DCs has yet to be examined in models such as $APC^{Min/+}$. The remarkable capacity of these cells to orchestrate distinct immune responses is aided by a panoply of environmental cues, which condition the cells to adopt specific phenotypes in different settings. DCs in gut-associated lymphoid tissue are of particular interest because they maintain tolerance to commensal flora as well as mount protective inflammatory responses in the face of pathogen incursion.

The experiments described in this report indicate that small intestine LPDCs (SI-LPDCs) play a critical role in the inflammatory process that underlies tumor progression in the $APC^{Min/+}$ mouse. Whereas SI-LPDCs in healthy control mice induce the formation of $T_{Regs}$, $APC^{Min/+}$ SI-LPDCs are reprogrammed to induce Th17 formation. A marked reduction in the intestine of the vitamin A metabolite, retinoic acid (RA), which under homeostatic conditions maintains the tolerogenic functions of LPDCs, explains the reprogramming of these cells. Since we find identical defects in RA metabolism in FAP tissue, the same mechanism that drives inflammation in $APC^{Min/}$ mice contributes to tumor formation in FAP.

Inflammatory DCs accumulate in the SI-LP of $APC^{Min/+}$ mice. We initially compared the frequency of DCs in various tissues in $APC^{Min/+}$ mice and their WT littermate controls. DCs were identified as $EpCAM^-CD45^+Lin^-MHCII^+CD11c^+$ and analyzed by flow cytometry at 10, 14 and 18 weeks of age, time points that correspond to minimal (<30 polyps, <2 mm diameter), intermediate (30-60 polyps, 0.5-4 mm diameter) and late stage (>60 polyps, 1-6 mm diameter) disease, respectively. As shown in FIG. 1*a-b*, DCs accumulated in the SI-LP as disease progressed. In the steady state, DCs in the gut environment are comprised of three phenotypically distinct populations—$CD103^+CD11b^-$, $CD103^+CD11b^+$ and $CD103^-CD11b^+$ DCs[16]. $CD103^+CD11b^-$ DCs are enriched in the Peyer's patches, whereas $CD103^+CD11b^+$ and $CD103^-CD11b^+$ DCs are found mainly in the LP[16]. Although there were some differences in the frequency of splenic DC subsets between $APC^{Min/+}$ and WT control mice, no significant differences in the percentages of the three key subsets were observed in the mesenteric lymph nodes (mLN), Peyer's Patches (PP) and most importantly, the SI-LP (FIG. 1*c*). These analyses were performed at intermediate stage, as the $APC^{Min/+}$ mice lose their Peyer's Patches by late stage disease, accompanying other developmental abnormalities such as early thymic involution, splenomegaly and lymphodepletion.

We considered the possibility that the DCs accumulating in the SI-LP of $APC^{Min/+}$ mice may be responsible for generating the altered $CD4^+$ T cell response in the gut demonstrated in previous studies. No significant changes in the expression of costimulatory molecules (CD40, CD80, CD83, CD86 or PDL1) were seen on these cells (FIG. 1*d*). Nonetheless, when stimulated with a panel of TLR agonists, purified SI-LPDCs from $APC^{Min/+}$ mice, especially those with late-stage disease, secreted much larger amounts of the pro-inflammatory cytokines TNF$\alpha$, IL-6 and IL-12p40 compared to SI-LPDCs from WT mice (FIG. 1*e*).

$APC^{Min/+}$ SI-LPDCs are impaired in their ability to induce $T_{Regs}$ and instead promote Th17 formation. To address whether $APC^{Min/+}$ SI-LPDCs are able to induce $Foxp3^+$ $T_{Regs}$ de novo, we cultured CFSE-labeled naïve $CD4^+CD62L^+Foxp3^-$ T cells from OT-II TCR transgenic mice with purified DCs in the presence of TGF$\beta$ and the ovalbumin$_{323-339}$ peptide. After 5 days of co-culture, the frequency of $Foxp3^+CD4^+$ T cells was determined. The results show that splenic DCs from both genotypes induced $Foxp3^+$ cells weakly, while mLN/PP DCs were more potent inducers of $Foxp3^+$ cells, consistent with previous studies. Interestingly, $APC^{Min/+}$ SI- LPDCs were impaired in their capacity to induce Foxp3$^+$ cells compared to WT controls (FIG. 2*a*, FIG. 7*a*). This impairment was observed beginning at intermediate stage and became more apparent at late stage (FIG. 7*c*). Similar results were obtained across a 25 fold range of peptide concentration (FIG. 2*b*, FIG. 7*b*).

When we measured the levels of key immunomodulatory cytokines in the supernatants of these DC-T cell co-cultures, the results revealed a striking six-fold reduction in IL-10 generated in APC$^{Min/+}$ LPDC co-cultures compared to the WT control cultures (FIG. 2*e*). Moreover, there was a concomitant and similarly dramatic increase in IL-17A (FIG. 2*f*), consistent with the documented role of Th17 cells in adenoma development. Intracellular staining of the T cells in the APC$^{Min/+}$ co-cultures confirmed the presence of IL-17A producing cells and a reduction of IL-10 producing cells.

As CD103$^+$ SI-LPDCs are the main cells responsible for generating immune tolerance in the intestinal environment, we sorted SI-LPDCs into CD103$^+$ and CD103$^-$ subsets to determine which subset accounted for the observed impairment in Foxp3 induction. APC$^{Min/+}$ CD103$^+$ SI-LPDCs were four-fold less able to induce Foxp3$^+$ T cells compared to their WT counterparts (FIG. 2*c*). In contrast, CD103$^-$ SI-LPDCs from both genotypes were equally poor in inducing Foxp3 expression (FIG. 2*c*), consistent with previous studies. In addition, co-cultures of APC$^{Min/+}$ CD103$^+$ SI-LPDCs and T cells, but not CD103$^-$ LPDC-T cell co-cultures, contained large amounts of IL-17A. These results show that the CD103$^+$ subset of SI-LPDCs in APC$^{Min/+}$ mice is not only responsible for defective induction of $T_{Regs}$, but also for the generation of Th17 cells.

Retinoic acid (RA) reverses the inflammatory phenotype of APC$^{Min/+}$ LPDCs. The unique capacity of the CD103$^+$ SI-LPDC subset to store and metabolize vitamin A into RA explains the specialized role of these cells in generating and maintaining intestinal tolerance. We hypothesized that the cytokine profile of the pro-inflammatory APC$^{Min/+}$ SI-LPDCs could be modulated by changes in the local RA concentration. To address this possibility we added RA or the RA receptor antagonist, LE540, to the LPDC-T cell co-cultures and assessed the induction of Foxp3$^+$ T cells. LE540 abrogated Foxp3 induction in both WT and APC$^{Min/+}$ SI-LPDC co-cultures (FIG. 2*d*), whereas RA enhanced Foxp3 induction in the APC$^{Min/+}$ SI-LPDC co-cultures to the levels seen in WT co-cultures (FIG. 2*d*). Addition of RA also strongly inhibited IL17A production in the APC$^{Min/+}$ co-cultures. Since Th17 differentiation requires IL-6 in conjunction with TGFβ, and since no exogenous IL-6 was added to our cultures, we postulated that the APC$^{Min/+}$ LPDC co-culture supernatants may contain IL-6. This was confirmed (FIG. 2*g*). RA also potently inhibited IL-10 production in both WT and APC$^{Min/+}$ co-cultures, consistent with a previous study.

Loss of RA is linked to both reduced expression of retinaldehyde dehydrogenases (Raldh) and defective regulation of the transcriptional co-repressor C-terminal binding protein 1 (Ctbp1). Vitamin A, or retinol, when absorbed in the intestine, is either converted to a storage form or metabolized to RA. In the latter, retinol is catalyzed to retinal by two families of enzymes, the alcohol dehydrogenases (ADHs) and the short-chain dehydrogenase reductases (RDH), and subsequently oxidized to bioactive RA by the Raldh enzymes. To ascertain whether APC$^{Min/+}$ LPDCs are able to produce RA, we used RT-qPCR to measure the expression of several key Raldh enzymes in these cells. In line with previous studies, Raldh expression in the SI-LP of both WT and APC$^{Min/+}$ mice was consistently higher than control splenic DCs (FIG. 3*b*). At early stage, APC$^{Min/+}$ SI-LPDCs expressed equal or higher levels of Raldh1a1 and Raldh1a2 compared to WT SI-LPDCs (FIG. 3*a*). However, as the disease progressed in APC$^{Min/+}$ mice, expression of these enzymes, especially Raldh1a1, declined markedly.

Recent studies have shown that RA in the gut induces Raldh expression. Since IECs constitutively express these retinol-metabolizing enzymes and can efficiently generate RA, we postulated that defective RA production in the IECs might help explain the loss of Raldh expression observed in the APC$^{Min/+}$ LPDCs. As shown in FIG. 3*b*, Raldh1a1 and Raldh1a2 expression in sorted CD45$^-$EpCAM$^+$ IECs did not change significantly through early and intermediate stage disease. At late stage, however, APC$^{Min/+}$ IECs exhibited approximately five- and two-fold reduction in the expression of Raldh1a1 and Raldh1a2, respectively, compared to WT IECs. Of note, compared to WT IEC, ADH class I and II expression in APC$^{Min/+}$ IEC increased at intermediate stage and decreased at subsequent late stage (FIG. 9). Taken together, these data show that both APC$^{Min/+}$ SI-LPDCs and IECs lose expression of the critical Raldh1a1 and Raldh1a2 enzymes by late stage disease, and have a reduced RA-production capacity compared to their WT counterparts.

To confirm that the changes observed at the transcript level of these enzymes correlated with a loss of RA in the local tumor milieu, we utilized tandem mass spectrometry to quantitatively profile endogenous retinoids in late stage APC$^{Min/+}$ duodenum, jejunum, ileum, colon and eye. As shown in FIG. 5*i*, RA levels in APC$^{Min/+}$ tissues were diminished compared to WT controls, with the difference reaching statistical significance in the ileum, where there is the highest frequency of polyps, and in the colon. Although retinol was reduced in the APC$^{Min/+}$ ileum, tissues from both genotypes had comparable amounts retinyl esters, indicating that the deficit in RA is not due to a lack of substrate (FIG. 10).

Previous studies have demonstrated that the APC protein can directly bind to Ctbp1 in both *Drosophila melanogaster* and human cell lines. APC-mutant zebrafish were shown to express abnormally high levels of Ctbp1, which correlated with low levels of the intestinal retinol dehydrogenase Rdh1I and intestinal differentiation defects. Moreover, reintroduction of the APC protein into human colon carcinoma cell lines led to a proteasome-dependent destruction of Ctbp1, concomitant with increased expression of the retinol dehydrogenase, DHRS9. To determine if the loss of RA we observed in the APC$^{Min/+}$ gut may be due to upregulation of Ctbp1, we assessed Ctbp1 transcript levels in SI-LPDCs and IECs. A significant elevation of Ctbp1 was seen in APC$^{Min/+}$ IECs compared to WT IECs beginning at intermediate stage disease (FIG. 3*c*). Surprisingly, there was a parallel accumulation of Ctbp1 in the APC$^{Min/+}$ SI-LPDCs as well. These findings suggest that along with loss of Raldh expression, elevated levels in Ctbp1 in both cell types may suppress intestinal retinol dehydrogenase expression, thereby contributing to the loss of RA observed in the tumor milieu.

FAP adenomas exhibit the same inflammatory changes and abnormalities in RA metabolism as seen in APC$^{Min/+}$ mice. To assess whether our findings in the APC$^{Min/+}$ model are predictive of the human condition, we used immunohistochemistry and immunofluorescence to analyze the colonic polyps of FAP patients. For comparison, we analyzed biopsies of normal colon as well as sessile serrated polyps (SSP), the latter serving as a source of non-APC mutated adenomas. IL17A expression was strikingly elevated in FAP adenomas compared to adjacent uninvolved colon, normal colon or SSP (FIG. 4*a*). Staining of the same tissues with an isotype control antibody is shown in FIG. 11. These findings indicate that the inflammatory environment in FAP polyps is similar to that seen in the $APC^{Min/+}$ mouse model.

We next examined the tissues for expression of key vitamin A metabolizing enzymes and the proteins that modulate them. Consistent with published reports, cytoplasmic β-catenin was expressed at higher levels in FAP adenomas compared to adjacent uninvolved tissue and to SSP. Interestingly, however, β-catenin was not expressed by cells expressing dendritic cell-specific Intercellular Adhesion Molecule-3-Grabbing Non-integrin (DC-SIGN) in the tissues tested (FIG. 4*b*). Ctbp1, the transcription factor that negatively regulates intestinal RDHs, was present at much higher concentration in FAP IECs than in the IECs of normal or SSP (FIG. 5*c*), consistent with previous reports, Remarkably, Raldh1a1 and Raldh1a2 expression was almost completely abolished in IECs of FAP adenoma tissue and not SSP (FIG. 5*d-e*), validating our findings in the $APC^{Min/+}$ mouse. Finally, the RA catabolizing enzyme CYP26A1 was markedly upregulated in the epithelia (FIG. 5*f*) as has been reported. Since FAP adenomas contain little RALDH activity (possibly due to excess Ctbp1), but excessive CYP26A1, the net result is likely a dearth of RA in the local tumor milieu.

Polyposis is exacerbated by a vitamin A deficient (VAD) diet and ameliorated by Liarozole, a CYP26A1 inhibitor. Mice fed a vitamin A-deficient diet have dramatically reduced DC Raldh expression. Given the likelihood that diminished RA explains the pro-inflammatory profile of SI-LPDCs in $APC^{Min/+}$ mice, we postulated that prolonged vitamin A-deficiency would intensify Raldh loss, drive inflammation and accelerate polyp development. To test this hypothesis, groups of WT and $APC^{Min/+}$ mice were placed on a diet containing no vitamin A for 10 weeks, beginning at 8-10 weeks of age, after which they were returned to a normal rodent chow diet. Groups of mice treated with Celecoxib (a cyclooxygenase-2 inhibitor) and Rosiglitazone (a peroxisome proliferator-activated receptor-γ agonist), were included as positive and negative controls, respectively. These compounds were added to "base" mouse chow which contained 4 IU vitamin A/g. Disease development and severity were monitored on the basis of survival, changes in body weight, hematocrit and polyp count at the point of euthanasia.

WT mice on each diet gained weight comparably (FIG. 12) and did not develop polyps. $APC^{Min/+}$ mice on the base diet survived throughout the 10-week period of disease monitoring, but all succumbed by week 24 (FIG. 5*a*). Compared to mice on the base diet $APC^{Min/+}$ mice treated with Celecoxib had markedly prolonged survival, while mice that received Rosiglitazone had reduced survival consistent with previous reports (FIG. 5*a*). Interestingly, VAD diet-fed $APC^{Min/+}$ mice had particularly aggressive disease and succumbed even more rapidly than mice on Rosiglitazone (FIG. 5*c-d*). The body weights of $APC^{Min/+}$ mice placed on base or VAD diets, or treated with Rosiglitazone, decreased comparably, while those treated with Celecoxib gained weight steadily (FIG. 5*b*).

Since decreasing RA in the intestinal environment exacerbates disease in $APC^{Min/+}$ mice, we wanted to test the hypothesis that increasing intestinal RA would ameliorate disease. Oral administration of RA was not feasible, since it is known to stimulate further polyp growth in $APC^{Min/+}$ mice due to the induction of CYP26A1 and consequent loss of RA. Instead, we sought to increase intestinal RA by preventing its breakdown with a CYP26A1 inhibitor, Liarozole, which was added to the base diet of 8 week old mice for a period of 10 weeks, as above. Remarkably, the Liarozole-treated mice exhibited a striking reduction in the number of polyps as well as a significant increase in body weight, although their hematocrits deteriorated to the same extent as untreated controls (FIG. 6*a-d*). To confirm that Liarozole mediated its effects by increasing local RA concentration in the intestine, we measured retinoid levels in the treated mice. As shown in FIG. 6*e*, RA levels returned to normal in Liarozole treated mice, especially in the ilium.

To assess whether the Liarozole mediated increase in intestinal RA influenced immune outcome by 're-reprogramming' the pro-inflammatory $APC^{Min/+}$ SI-LPDCs, SI-LPDCs from Liarozole-treated mice were isolated and tested functionally. The results show that $APC^{Min/+}$ SI-LPDCs from Liarozole-treated miceno longer produced substantial amounts of pro-inflammatory cytokines when stimulated with TLR agonists (FIG. 6*f*), and instead of inducing Th17 formation, promoted the formation of IL-10 secreting Foxp3+ Tregs (FIG. 6*g-h*) at levels similar to wildtype mice. Taken together, these findings show that whereas exacerbating RA deficiency in the intestine accelerates disease, restoring RA reverses the reprogramming of SI-LPDCs, thereby preventing deleterious Th17 responses and ameliorating disease.

The role of intestinal inflammation in the development of adenomas in the $APC^{Min/+}$ model of spontaneous neoplasia has been well documented. However, the few immunological studies performed on $APC^{Min/+}$ mice and related APC mutation models have focused almost exclusively on altered T cell responses, with no attention directed at the underlying cause of these changes. Our findings indicate that as disease progresses, there is an accumulation of pro-inflammatory DCs in the SI-LP that induce the formation of Th17 cells. This stands in dramatic contrast to the SI-LPDCs of healthy mice, which do not promote inflammation but instead maintain immune tolerance through the generation of $T_{Regs}$. CD103+ LPDCs, believed to be responsible for tolerance induction in the intestine, were present in greater numbers in $APC^{Min/+}$ than healthy control mice, but secreted pro-inflammatory cytokines and induced the formation of Th17 cells rather than $T_{Regs}$. The induction of Th17 cells by $APC^{Min/+}$ SI-LPDCs likely represents a critical control point in shaping the inflammatory milieu that drives tumor growth, and explains the predominance of IL-17 in the inflamed $APC^{Min/+}$ intestine.

Since SI-LPDCs play such an important role in tumor-promoting inflammation, identifying the mechanism that induces their unusual phenotype in $APC^{Min/+}$ mice is key to understanding how the inflammatory cascade is triggered. We hypothesized that these cells could have undergone reprogramming in response to one or more factors in the tumor microenvironment. Our efforts focused on RA because of the well documented role of this molecule in maintaining a tolerant state in the intestine. Addition of RA to the $T_{Reg}$ induction cultures not only enhanced the capacity of $APC^{Min/+}$ SI-LPDCs to induce Foxp3+ T cells but also prevented the induction of Th17 cells. Conversely, addition of the RAR antagonist, LE540, resulted in further diminution of Foxp3 induction and augmented the production of IL17A by more than five-fold.

The absolute amount of RA in the intestines of mice with APC mutations has not been reported previously, likely due to the technical difficulty of carrying out such measurements. By preventing exposure of tissues to white light, which rapidly degrades retinoids, and utilizing mass spectroscopy to measure RA, we could achieve accurate RA quantitation. Our results revealed highly significant reductions of RA in the ileum and colon of $APC^{Min/+}$ mice, but not in other sites. Although some RA remained in the intestines, the reductions seen are nonetheless noteworthy, as retinol bound to its specific retinol-binding protein (RBP) is strictly regulated and maintained in plasma at about 2 μM despite daily fluctuations in dietary intake of vitamin A. Only in situations of severe, prolonged vitamin A-deficiency, where stores of retinyl esters in the liver are depleted, is there a drop in plasma concentration of retinol-RBP, and by association, RA.

The loss of RA in the tumor milieu appears to be due to both diminished synthesis and excessive breakdown of this molecule. We found that the critical Raldh enzymes that control RA production decline as disease progresses, and this is likely explained, in part, by the overexpression of Ctbp1, which suppresses Rdh., Ctbp1 is normally degraded by APC, but accumulates in the absence of functional APC. Our immunofluorescence data confirmed a marked accumulation of Ctbp1 in FAP IECs. Inactivation of the APC gene also results in constitutive expression of β-catenin, which upregulates the major RA catabolic enzyme, CYP26A1. Indeed, the CYP26A1 transcript has been found to be upregulated in whole tissue isolated from both $APC^{Min/+}$ and FAP adenomas, sporadic colorectal carcinomas, and the intestine of APC-mutant zebrafish embryos. Here we validate these observations, specifically identifying epithelial cells as one of perhaps several cell types in FAP colon displaying CYP26A1 upregulation. Finally, prostaglandin E2 (PGE2), which has been reported to inhibit Raldh1a2 expression in DCs, may contribute to the loss of RA. It is well established that FAP and $APC^{Min/+}$ epithelium exhibit constitutively high Cox2 expression. In addition, we found that the Cox2 transcript is overexpressed in late stage $APC^{Min/+}$ SI-LPDCs compared to their WT counterparts (FIG. 13). This finding is consistent with the possibility that Cox2-overexpression and abundance of PGE2 in the FAP colon may lead to suppression of Raldh1a2 in both DCs and epithelia. Taken together, our results point to at least 3 mechanisms that cooperate to suppress the RA levels in the tumor milieu of $APC^{Min/+}$ mice. Moreover, these data indicate that the APC mutation underlying malignant transformation of intestinal epithelia is directly linked to the immune defect driving tumor growth. We summarize our key findings and others in an illustration depicted in FIG. 6*d*.

Importantly, human FAP adenoma tissue exhibited several of the same defects that we found in the $APC^{Min/+}$ mouse intestine. Not only was there a marked elevation in IL17 expression, signifying Th17 driven inflammation, but in addition we observed concomitant Raldh downregulation and CYP26A1 upregulation in colonic epithelial cells. Defective RA production combined with enhanced RA breakdown would produce a deficit of similar magnitude to that seen in $APC^{Min/+}$ mice.

To investigate the role of RA in disease development and progression, we sought to alter RA concentration in the intestine in vivo, by removing or administering molecules in the diet that are known to affect RA production or breakdown. Our results revealed that a diet deficient in Vitamin A exacerbates disease, while the CYP26A1 inhibitor, Liarozole, ameliorates disease as indicated by a dramatic reduction in the number of intestinal as well as steady weight gain.

Since increasing intestinal RA proved highly efficacious in $APC^{Min/+}$ mice, doing so in patients with APC-mutation associated bowel disease may be initiated. Small molecule agonists of Rdhs and Raldhs, or inhibitors of CYP26 such as Liarozole, are logical candidates. Indeed, Liarozole has been evaluated in clinical trials for diseases unrelated to colorectal cancer and is apparently well-tolerated. Maintaining sufficient RA in the intestinal environment could therefore, reverse inflammation and reduce tumor burden, as we observed in $APC^{Min/+}$ mice.

Materials and Methods

Mice. Breeding pairs of $APC^{Min/+}$ male and WT C57BL/6 female mice were purchased from The Jackson Laboratory and bred on-site. OT-II TCR transgenic $Rag^{-/-}$ mice were purchased from Taconic. $TNF^{\Delta ARE/+}$ mice were kindly provided by Dr. Frank Jirik of the University of Calgary, Canada. All mice were housed in an American Association for the Accreditation of Laboratory Animal Care-accredited animal facility, maintained in pathogen-free conditions on a standard rodent chow ad libitum unless otherwise stated.

Isolation of DCs. Epithelial cells from the small intestine were washed in PBS with vigorous stirring and the remaining intestinal pieces digested twice with Type VIII Collagenase (Sigma-C2139) and DNase I (Sigma). Spleen and mesenteric lymph nodes were digested with collagenase Type IV (Worthington, 200 U/ml). For purification of DCs, cells were stained with monoclonal antibodies (Biolegend) against CD45.2, CD49b, CD3e, CD19, CD11c, MHC II, EpCAM and propidium iodide (PI), and sorted using a FACS Aria (BD Biosciences). In some cases, DCs were additionally sorted using anti-CD103.

Flow Cytometric analysis. Isolated small intestine lamina propria (SI-LP) cells, splenocytes and mesenteric lymph node cells were resuspended in 1% BSA in PBS (FACS buffer). After Fc blockade with anti-FcγRIII/II (BD Biosciences), cells were stained with Live/Dead Blue (Invitrogen) or PI, and monoclonal antibodies (all Biolegend) against CD40, CD80, CD83, CD86, PDL1, Thy1.2 and CD4. Intracellular Foxp3 and cytokines were stained using antibodies against Foxp3, IL10, IL6, IL17A (all eBioscience) per manufacturer's instructions. Flow cytometric analysis was performed on a LSRII flow cytometer (BD Biosciences).

T cell differentiation assay. $2\times10^4$ sorted $CD11c^{high}$ MHCII+ DCs were co-cultured with $1\times10^5$ MACS-enriched CD4+CD62L+Foxp3− naïve T cells from the spleen and lymph nodes of OT-II TCR-transgenic mice, along with $OVA_{323-339}$ peptide (New England Peptide) and 10 ng/ml recombinant human TGF-β1 (Peprotech). On day 5, cells were harvested and analyzed for intracellular Foxp3 or intracellular cytokines. In some experiments, cells were restimulated on day 4 with 1 μg/ml each of plate-bound anti-CD3 and anti-CD28 (BD Biosciences), with or without Brefeldin A for 18 hr. Where indicated, 10 nM all-trans RA (Sigma), or 1 μM LE540 (Wako Chemicals) was added to culture wells.

ELISA. Purified SI-LP DCs were stimulated for 48 hr with Toll-like receptor agonists—1 μg/ml Pam3Csk4, 10 μg/ml Poly I:C, 10 μg/ml LPS, 1 μg/ml flagellin, 10 μg/ml R848, 10 μg/ml CpG 2336 (Invivogen). Supernatants from these experiments were assayed for IL-6, TNFα, IL12-p40 and those from were DC-T cell co-cultures were assayed for IL-6, IL-10 and IL17A, performed according to manufacturer's instructions (eBioscience).

Quantitation of gene expression using real-time PCR. Total RNA from purified LP DCs, splenic DCs and epithelial cells was extracted using RNAeasy kits (Qiagen), and the DNase-treated total RNA was reverse-transcribed using High-Capacity Reverse Transcription Kit (Applied Biosystems) according to manufacturer's instructions. Gene expression of ADH class I-III, Raldh1a1-3, Ctbp1, and Cox2 was determined by quantitative PCR with Power SYBR Green PCR Master Mix (Applied Biosystems) per manufacturer's instructions using a 7900HT real-time PCR instrument (Applied Biosystems). Ubiquitin levels were measured in a separate reaction and used to normalize the data.

Quantitation of tissue retinoids. Retinyl esters (RE), all-trans retinol, and all-trans retinoic acid (RA) were extracted from the duodenum, jejunum, ileum, colon and eye using procedures to those described previously. RA was quantified by LC/MS/MS with atmospheric pressure chemical ionization. RE and retinol were quantified by HPLC. Tissues were harvested and retinoids handled under yellow light using only glass laboratory equipment. Results were normalized to per gram tissue weight, or to control groups as fold-change.

Histology.

Immunohistochemistry.

Formalin-fixed, paraffin-embedded, 5 μM-thick, human tissue sections were stained with the primary antibody rabbit IL17A (Protein Tech Group (PTG) 13082-1-AP), and the secondary rabbit-HRP polymer (Dako Envision). Antigen retrieval was performed using Human Diva Decloaker citrate buffer (Biocare Medical).

Immunofluorescence.

Primary antibodies, all from PTG and rabbit anti-human unless otherwise noted, were mouse DC-SIGN (Dendritics DDX0202), β-catenin (51067-2-AP), Ctbp1 (Human Protein Atlas (HPA) HPA018987), Raldh1a1 (15910-1-AP), Raldh1a2 (HPA010022), CYP26A1 (HPA C6498). Chicken secondary antibodies include anti-rabbit Alexa647 and anti-mouse Alexa488 (Invitrogen). 11 normal colon, 8 FAP adenoma, 2 FAP adenocarcinoma and 4 sessile serrated polyp patients were analyzed. Images were collected using a Leica DM2500 confocal laser scanning microscope, and analyzed using the LAS AF software.

Drug Treatment.

1500 ppm of Celecoxib (Celebrex, Pfizer), 100 ppm of Rosiglitazone (Avandia, Glaxo Smith Kline), or 40 ppm of Liarozole (Tocris Pharmaceuticals) was incorporated into a base diet (4 IU/g of vitamin A) by Research Diets. A vitamin A deficient (0 IU/g) diet (VAD) was also studied. Hematocrits were measured every 2 weeks, while weights and DAI were measured every week. At the point of euthanasia, polyps were enumerated and measured using a stereomicroscope at 10× magnification, from the gastro-duodenual junction to the ceco-colic junction.

Statistics.

An unpaired student's t test (2-tailed) with a 95% confidence interval was performed in Prism (Graphpad) in all experiments unless otherwise stated. Kaplan-Meier survival curves were analyzed with the log-rank test. Differences of DAI in the drug treatment studies were analyzed using the Wilcoxon Rank-Sum test in R. Where needed, mean±SEM was represented on graphs. $P<0.05=*$; $p<0.001=$; $p<0.0001=*$.

Example 2

Drug Treatment of Inflammatory Bowel Disease

Inflammatory DCs that infiltrate the GALT during autoimmune colitis appear to amplify Th17 responses that exacerbate intestinal pathology, similar to our observations in the $APC^{Min/+}$ model of intestinal cancer. To address whether the loss of local RA as observed in our studies extended beyond APC-associated GI cancers, we quantified endogenous tissue retinoids as before in $TNF^{\Delta ARE/+}$ and azoxymethane/dextran-sodium-sulphate (AOM/DSS)-treated mice. A model of Crohn's disease that exhibit chronic ileitis, $TNF^{\Delta ARE/+}$ mice provide a model to examine whether there was a similar RA deficiency in cases of generalized chronic intestinal inflammation. The AOM/DSS carcinogen and mucosal injury-induced model of colorectal carcinogenesis provided another model of colorectal cancer, which is chemically-induced instead of spontaneously-arising, like the $APC^{Min/+}$. Intriguingly, compared to WT tissue, we observed a marked reduction in RA in both the ileum and colon of $TNF^{\Delta ARE/+}$ and AOM/DSS mice, corresponding to the very locations where inflammation and carcinoma was occurring respectively.

Taken together, an RA deficiency can occur in generalized settings of chronic intestinal inflammation and in colorectal cancer, suggesting that the beneficial effects of modulation of local intestinal RA levels extends to generalized chronic inflammation in the gut.

As with many other hormones and vitamins that can be dysregulated in disease, reinstating RA to the appropriate dynamic range may be key. RA has a short elimination half-life in vivo and in cultured cells just 6-7 hours. Retinol bound to its specific retinol-binding protein in plasma is strictly regulated and maintained at about 2 μM despite daily fluctuations from dietary intake of vitamin A. Only in situations of severe vitamin A-deficiency where stores of retinyl esters in the liver are depleted, is there a drop in plasma concentration of retinol-RBP. Corresponding RA levels in plasma are in the range of 5-10 nM, more than two orders of magnitude lower than that of its substrate retinol, reinforcing the notion that retinol metabolism is tightly regulated and often restricted to certain settings. Local RA concentrations in the $APC^{Min/+}$ ileum and colon may be reduced to a point where tolerance is broken, but not to the point where compensatory mechanisms that maintain tolerance in severe RA deficiency starts to kick in; or to the point that Th17 cells cannot induce inflammation anymore.

We measured RA levels in Liarozole-treated $APC^{Min/+}$ mice and observed a return to wildtype levels of RA in the ileum, so we validated that Liarozole did indeed increase local concentrations of RA to homeostatic levels, and not to supraphysiological levels.

Since decreasing RA in the intestinal environment exacerbates disease in $APC^{Min/+}$ mice, we tested the reciprocal hypothesis that increasing intestinal RA would ameliorate disease. RA was administered intraperitoneally (i.p.) twice weekly for 6 weeks to APCMin/+ mice, using the same protocol that has been reported to attenuate ileitis in a mouse model of Crohn's disease. Surprisingly, compared to controls, this regimen did not improve disease outcome in terms of tumor frequency, body weight or hematocrit. Consistent with these findings, SI-LPDCs isolated from $APC^{Min/+}$ mice that received RA i.p. retained their proinflammatory phenotype and ability to induce the formation of Th17 cells. A likely explanation for this apparent paradox is that RA i.p. did not increase RA levels in the ileum, due to persistent breakdown of RA from upregulated CYP26A1 in $APC^{Min/+}$ tissue. Indeed, direct RA supplementation via the diet has been shown to stimulate tumor formation in the $APC^{Min/+}$ model.

Given these results, we decided to try an alternative strategy to increase intestinal RA by targeting the upregulated CYP26A1 with Liarozole, an inhibitor of this enzyme. Compared to untreated and RA i.p.-treated mice, Liarozole treated mice exhibited a striking reduction in tumor number in the jejunum and ileum (FIG. 14*a*), as well as a substantial increase in body weight (FIG. 14*b*), and hematocrit (FIG. 14*c*). Importantly, Th17 cells were reduced to WT levels (FIG. 14*e*), and SI-LPDCs from these mice failed to induce Th17 cells, instead promoting the formation of IL-10-secreting CD4+ T cells (FIG. 14*f*). Moreover, RA in the ileum of Liarozole-treated mice was restored to WT levels (FIG. 145*d*), likely explaining the therapeutic effect. Consistent with this interpretation, treatment of $APC^{Min/+}$ mice with Talarozole, a more potent and more specific CYP26A1 inhibitor than Liarozole 38, also ameliorated disease (FIG. 15).

Taken together, these findings indicate that whereas increasing the RA deficit in the intestine exacerbates disease, restoring RA to normal levels reverses the pro-inflammatory phenotype of SI-LPDCs, attenuates Th17-driven inflammation and ameliorates disease.

Example 3

Inflammatory DCs Accumulate in the SI-LP of $APC^{Min/+}$ Mice and Promote Th17 Formation and Tumor Growth The frequency of DCs in various tissues was compared in $APC^{Min/+}$ mice and their WT littermate controls. DCs (PI-EpCAM$^-$CD45$^+$Lin$^-$CD11$^{chi}$MHCII$^+$) were analyzed at 10, 14 and 18 weeks of age, which correspond to early—(<30 adenomas, <2 mm diameter), intermediate—(30-60 adenomas, 0.5-4 mm diameter) and late-stage (>60 adenomas, 1-6 mm diameter) disease, respectively. DCs accumulated in the SI-LP as disease progressed and by intermediate stage the frequency of SI-LPDCs was more than 3 times greater in $APC^{Min/+}$ than WT mice.

In the steady state, DCs in the gut consist of three phenotypically distinct populations: CD103$^+$CD11b$^-$, CD103$^+$ CD11b$^+$ and CD103$^-$CD11b$^+$ DCs. Although there were some differences in the frequencies of splenic DC subsets between $APC^{Min/+}$ and WT control mice, no significant differences in the percentages of the three main DC subsets were observed in the mesenteric lymph nodes (mLN)/Peyer's Patches (PP) or SI-LP. These analyses were performed at intermediate-stage, as $APC^{Min/+}$ mice lose their Peyer's Patches by late-stage disease. Further studies of SI-LPDCs from $APC^{Min/+}$ mice revealed that, although their expression of costimulatory molecules was similar to that of WT SI-LPDCs, they secreted much higher levels of the pro-inflammatory cytokines TNFα, IL-6 and IL-12p40 under basal conditions and in response to a panel of Toll-like receptor agonists. Moreover, $APC^{Min/+}$ SI-LPDCs induced fewer Foxp3$^+$ TRegs in a conventional TReg induction assay. This impairment was observed at intermediate-stage and became even more apparent at late-stage disease. Similar results were obtained across a 25-fold range of peptide concentrations. Splenic DCs from both genotypes weakly induced Foxp3$^+$ T cells, while mLN/PP DCs were more potent inducers of Foxp3$^+$ T cells, consistent with previous studies.

Supernatants obtained from $APC^{Min/+}$ SI-LPDC-T cell co-cultures contained a striking six-fold reduction in IL-10 compared to WT SI-LPDC co-cultures. Moreover, there was a concomitant and similarly dramatic increase in IL-17A, a key cytokine involved in adenoma development. Since Th17 differentiation requires IL-6 in addition to TGFβ and no exogenous IL-6 was added to our cultures, we measured IL-6 in co-culture supernatants and, as expected, there were larger amounts in $APC^{Min/+}$ SI-LPDC co-cultures. Consistent with these findings, IL-23, known to be essential for the maintenance of Th17 cells, though not detectable by ELISA, was expressed at higher levels in $APC^{Min/+}$ SI-LPDCs compared to WT cells in situ.

As CD103$^+$ SI-LPDCs are the main cells responsible for generating immune tolerance in the intestinal environment, we sorted SI-LPDCs into CD103$^+$ and CD103$^-$ subsets to assess the role of each subset in the observed impairment in Foxp3 induction. $APC^{Min/+}$ CD103$^+$ SI-LPDCs were four-fold less efficient at inducing Foxp3$^+$ T cells compared to their WT counterparts. In contrast, CD103$^-$ SI-LPDCs from both genotypes were equally poor at inducing Foxp3 expression. Both CD103$^-$ and CD103$^+$ $APC^{Min/+}$ SI-LPDCs induced more Th17 cells compared to the WT SILPDC subsets. These results show that the CD103$^+$ subset of SILPDCs in $APC^{Min/+}$ mice is responsible for the observed defect in TReg induction, and that both CD103$^-$ and CD103$^+$ SI-LP-DCs likely contribute to the Th17-skewed inflammation observed in these mice.

To directly assess the role of DCs in tumor progression, we generated bone marrow (BM) chimeras to selectively and constitutively ablate DCs using BM donor cells in which Diphtheria Toxin A (DTA) is activated in CD11c expressing cells. Chimeras generated with WT and $APC^{Min+}$ BM were used for comparison. Depletion of DCs resulted in a significant decrease in total tumor number, due mainly to a marked tumor reduction in the ileum where the incidence of tumors in $APC^{Min/+}$ mice is highest, providing strong evidence that DCs are a key driver of tumor development. In contrast, $APC^{Min/+}$ mice reconstituted with WT BM had similar numbers of tumors compared to control $APC^{Min/+}$ BM-reconstituted $APC^{Min/+}$ mice, suggesting that the intestinal environment of the $APC^{Min+}$ host overrides any potential benefit afforded by a reconstituted WT immune system.

Example 4

Tissue Histology

Immunohistochemical and immunofluorescence staining of intestinal biopsies from FAP and $APC^{min}$ mice shows the presence of identical markers of inflammation as well as abnormal RA metabolism, including Raldh1a1, Raldh1a2 and CYP26A1. These findings support the view that the underlying pathology in $APC^{min}$ disease is similar to that of FAP. Tumors in the $APC^{min}$ model are primarily in the small intestine, whereas the tumors in FAP are primarily in the colon. One reason for this difference is that the mouse colon has very few DCs, while DCs are abundant in the human colon. Drugs that work in $APC^{min}$ mice also work in FAP, providing additional evidence that the pathogenesis of disease is the same in the two species.

Patients with ulcerative colitis, a type of inflammatory bowel disease, are at greatly increased risk for developing colon cancer due to the presence of chronic inflammation. Once regions of microscopic dysplasia are identified in the colons of such patients, the colons are typically removed because dysplasia almost always becomes cancer.

Based on staining data, the same abnormalities in retinoic acid metabolism that were found in $APC^{min}$ mice, patients with FAP and mice with experimentally induced colitis and Crohn's disease were present in the dysplastic areas of patients with ulcerative colitis.

What is claimed is:

1. A method of reducing chronic intestinal inflammation in an individual with familial adenomatous polyposis (FAP), the method comprising:

administering to the individual an effective dose of an agent that increases local concentration of retinoic acid (RA) through modifying enzymatic pathways involved in RA metabolism, wherein the agent is not retinoic acid, and wherein inflammation is reduced.

2. The method of claim 1, wherein the agent inhibits activity of a retinoic acid catabolizing enzyme.

3. The method of claim 1, wherein the agent increases activity of retinaldehyde dehydrogenase or retinol dehydrogenase in intestinal tissues.

4. The method of claim 2, wherein the retinoic acid catabolizing enzyme is a protein of the CYP26 family.

5. The method of claim 1, wherein the agent is orally administered.

6. The method of claim 4, wherein the retinoic acid catabolizing enzyme is CYP26A1.

7. The method of claim 6, wherein the agent comprises one or more of: liarozole, talarozole, ketoconazole, [S—(R*, R*)]—N-[4-[2-(dimethylamino)-1-(1H-imidazole-1-yl)propyl]-phenyl]2-benzothiazolamine (R116010), and (R)—N-[4-[2-ethyl-1-(1H-1,2,4-triazol-1-yl)butyl]phenyl]-2-benzothiazolamine (R115866).

8. The method of claim 7, wherein the agent comprises one or more of: liarozole and talarozole.

* * * * *